US009522856B2

(12) United States Patent
Venter et al.

(10) Patent No.: US 9,522,856 B2
(45) Date of Patent: Dec. 20, 2016

(54) PROCESS FOR OLIGOMERISING A HYDROCARBON TO FORM AT LEAST ONE CO-MONOMER PRODUCT

(71) Applicant: SASOL TECHNOLOGY (PROPRIETARY) LIMITED, Johannesburg (ZA)

(72) Inventors: Denise Louisette Venter, Vanderbijlpark (ZA); Kenny Tenza, Vaalpark (ZA); Palesa Nongodlwana, Alberton (ZA); Matthew James Overett, Bassonia (ZA); Kevin Blann, Alberton (ZA); Nicolaus Ladislaus Stark, Vereeniging (ZA); Craig McGregor, Sasolburg (ZA); Richard Neil Walsh, Vanderbijlpark (ZA)

(73) Assignee: SASOL TECHNOLOGY (PROPRIETARY) LIMITED (ZA)

( * ) Notice: Subject to any disclaimer, the term of this patent is extended or adjusted under 35 U.S.C. 154(b) by 80 days.

(21) Appl. No.: 14/398,948

(22) PCT Filed: May 8, 2013

(86) PCT No.: PCT/IB2013/053687
§ 371 (c)(1),
(2) Date: Nov. 4, 2014

(87) PCT Pub. No.: WO2013/168099
PCT Pub. Date: Nov. 14, 2013

(65) Prior Publication Data
US 2015/0126790 A1 May 7, 2015

(30) Foreign Application Priority Data
May 9, 2012 (ZA) ................................ 2012/03387

(51) Int. Cl.
*C07C 2/36* (2006.01)
*C07C 2/32* (2006.01)

(52) U.S. Cl.
CPC . *C07C 2/32* (2013.01); *C07C 2/36* (2013.01); *B01J 2219/00006* (2013.01); *C07C 2531/22* (2013.01); *C07C 2531/24* (2013.01); *C07C 2531/34* (2013.01); *Y02P 20/582* (2015.11)

(58) Field of Classification Search
CPC ............ C07C 2/36; C07C 2/32; C07C 11/107; C07C 11/02; C07C 2531/24; C07C 2531/34; C07C 2531/22; Y02P 20/582; B01J 2219/00006
See application file for complete search history.

(56) References Cited

U.S. PATENT DOCUMENTS

2007/0185362 A1  8/2007  Lattner et al.

FOREIGN PATENT DOCUMENTS

EP       0668105 A2    2/1995

OTHER PUBLICATIONS

Patent Cooperation Treaty, International Searching Authority, Search Report and Written Opinion for PCT/IB2013/053687, 9 pages, Sep. 24, 2013.

*Primary Examiner* — Nathan M Nutter
(74) *Attorney, Agent, or Firm* — Viksnins Harris & Padys PLLP

(57) ABSTRACT

A process (10) for oligomerising a hydrocarbon to form at least one co-monomer product (22) includes feeding a hydrocarbon reactant and organic liquid diluent solvent (32) into an oligomerisation reactor (12). The organic liquid diluent solvent has a normal boiling point below the normal boiling point of 1-hexene but above −20° C., or the organic diluent solvent is in the form of a solvent admixture with at least 70% by mass of the solvent admixture constituting organic diluent solvents having a normal boiling point below the normal boiling point of 1-hexene but above −20° C. The oligomerisation reactor (12) holds at least one co-monomer product formed in the oligomerisation reactor admixed with a catalyst system (25) introduced into the oligomerisation reactor (12). The catalyst system (25) includes a catalyst dissolved in at least one catalyst solvent. At least a portion of the hydrocarbon reactant is oligomerised in the reactor (12) to form co-monomer product and polymeric by-product as part of a liquid product, which is withdrawn. When there is only one catalyst solvent and only one organic liquid diluent solvent, the catalyst solvent and the organic liquid diluent solvent are not the same solvent. When there is more than one catalyst solvent or more than one organic liquid diluent solvent, at least one of the catalyst solvents is not also used as organic liquid diluent solvent or at least one of the organic liquid diluent solvents is not also used at the catalyst solvent. The mass ratio of all organic liquid diluent solvent introduced into the oligomerisation reactor to all catalyst solvent introduced into the oligomerisation reactor over a selected time period is between 15:1 and 4500:1.

14 Claims, 7 Drawing Sheets

PROCESS FOR OLIGOMERISING A HYDROCARBON TO FORM AT LEAST ONE CO-MONOMER PRODUCT

RELATED APPLICATIONS

Figure 1:
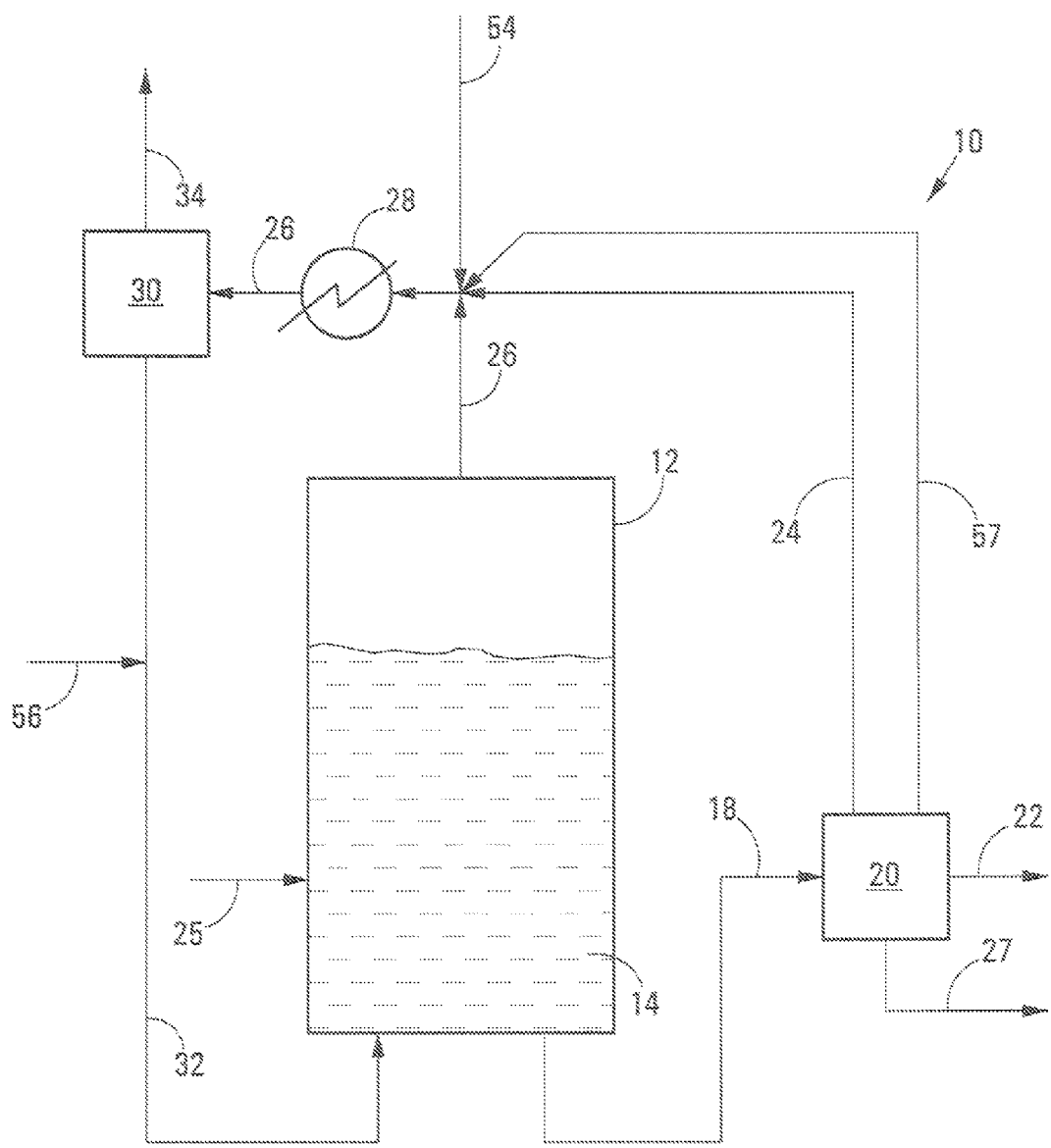

This application is a 371 of PCT/IB2013/053687 filed on 8 May 2013 which claims priority to South African Patent Application No. 2012/03387 filed on 9 May 2012. The entire contents of the foregoing are incorporated herein by reference.

THIS INVENTION relates to a process for oligomerising a hydrocarbon to form at least one co-monomer product.

A reaction solvent or diluent solvent, i.e. an inert liquid component or mixture of inert liquid components which does not take part in an oligomerisation reaction and which is not required to ensure that the oligomerisation reaction takes place, is normally used for the oligomerising, e.g. tetramerisation, of a hydrocarbon such as ethylene, to reduce secondary incorporation of alpha monomer or co-monomer products, e.g. 1-hexene or 1-octene, into less valuable longer chain products, by diluting the concentration of the primary oligomerisation reaction product or products. This diluent solvent may be distinguished from a catalyst solvent which is typically required to dissolve components of a catalyst system required for the oligomerising process.

A catalyst solvent in a process for oligomerising a hydrocarbon to form an alpha monomer or co-monomer product is thus a liquid component in which one or more catalyst precursor components (e.g. active metal precursor, ligand or catalyst activator) are dissolved so as to facilitate catalyst transport from a catalyst feed supply into a bulk liquid phase in which the oligomerisation typically takes place.

Typical aliphatic diluent solvents that have been considered in the past include iso-octane, cyclohexane and methylcyclohexane, all having boiling points intermediate that of 1-hexene and 1-octene. Propane as diluent solvent and evaporative cooling medium and which has a normal boiling point of −42.1° C., i.e. far below that of 1-hexene, has also been proposed.

Recovery of the diluent solvent for recycle is energy intensive.

It is believed that careful selection of an appropriate diluent solvent may have significant and unexpected advantages, e.g. relating to a reduction in energy consumption and catalyst selectivity in a process for oligomerising a hydrocarbon.

According to the invention, there is provided a process for oligomerising a hydrocarbon to form at least one co-monomer product, the process including
  feeding a hydrocarbon reactant and organic liquid diluent solvent into an oligomerisation reactor which is at an elevated pressure above atmospheric pressure, said organic liquid diluent solvent having a normal boiling point below the normal boiling point of 1-hexene but above −20° C., or said organic diluent solvent being in the form of a solvent admixture with at least 70% by mass of the solvent admixture constituting organic diluent solvents having a normal boiling point below the normal boiling point of 1-hexene but above −20° C., and said oligomerisation reactor holding at least one co-monomer product formed in the oligomerisation reactor admixed with a catalyst system introduced into the oligomerisation reactor, said catalyst system including a catalyst dissolved in at least one catalyst solvent to facilitate introducing said catalyst system into the oligomerisation reactor;
  oligomerising at least a portion of the hydrocarbon reactant in the reactor to form said at least one co-monomer product and polymeric by-product as part of a liquid product with the liquid product thus including organic liquid diluent solvent, said at least one co-monomer product, said catalyst system, unreacted hydrocarbon reactant and said polymeric by-product; and
  withdrawing liquid product which includes organic liquid diluent solvent, said at least one co-monomer product, said catalyst system, unreacted hydrocarbon reactant and said polymeric by-product from the reactor,
  wherein, when there is only one catalyst solvent and only one organic liquid diluent solvent, said catalyst solvent and said organic liquid diluent solvent are not the same solvent, and when there is more than one catalyst solvent or more than one organic liquid diluent solvent, at least one of the catalyst solvents is not also used as organic liquid diluent solvent or at least one of the organic liquid diluent solvents is not also used at the catalyst solvent, and wherein the mass ratio of all organic liquid diluent solvent introduced into the oligomerisation reactor to all catalyst solvent introduced into the oligomerisation reactor over a selected time period is between 15:1 and 4500:1.

In this specification, in order to be consistent and to distinguish the diluent solvent for the hydrocarbon reactant from the catalyst solvent, the diluent solvent is generally referred to as the organic liquid diluent solvent. It is however to be appreciated that the organic liquid diluent solvent will not always be in liquid form, even though it may be referred to as the organic liquid diluent solvent.

The oligomerisation process of the invention is typically a continuous process, in contrast to a batch process.

Preferably, the mass ratio of all organic liquid diluent solvent introduced into the oligomerisation reactor to all catalyst solvent introduced into the oligomerisation reactor is between 150:1 and 1500:1, most preferably between 500:1 and 1500:1. In other words, for example, for a ratio of 1000:1, if 1000 kg of organic liquid diluent solvent (whether fresh or recycled) is fed over a selected time period of 1 hour into the oligomerisation reactor, 1 kg of catalyst solvent (whether fresh or recycled) is fed into the oligomerisation reactor over the same period. Naturally, the selected time period should be long enough to allow the oligomerisation reactor to reach or to operate at a substantially steady state.

The process preferably includes feeding the organic liquid diluent solvent into the oligomerisation reactor, such that the mass fraction of the organic liquid diluent solvent in said liquid product on a hydrocarbon reactant free basis is maintained between about 0.4 and about 0.8, more preferably between about 0.4 and about 0.7, most preferably between about 0.45 and about 0.6.

As will be appreciated, the diluent solvent may thus consist of a single organic liquid diluent solvent, or it may be in the form of an admixture of more than one organic liquid diluent solvent. Similarly, the catalyst system may include a single catalyst solvent, or it may include an admixture of catalyst solvents. When a single organic liquid diluent solvent and a single catalyst solvent are present, they are different. When more than one organic liquid diluent solvent and more than one catalyst solvent are present, at least one of the organic liquid diluent solvents is not also used as a catalyst solvent, or at least one of the catalyst solvents is not also used as organic liquid diluent solvent.

Preferably, at least 80% by mass, more preferably at least 90% by mass, most preferably substantially all of the organic liquid diluent solvent has a normal boiling point below the normal boiling point of 1-hexene but above −20° C.

The polymeric by-product may include oligomeric by-product. For simplicity, the specification hereinafter refers to polymeric by-product, but it is to be noted that the intention is that a reference to polymeric by-product is a reference to polymeric by-product which may include oligomeric by-product, and which may include a plurality of different polymers and/or oligomers.

The reactor may hold a bulk liquid phase which includes the liquid product. The organic liquid diluent solvent may be selected to increase the solubility of a liquid hydrocarbon reactant in the bulk liquid phase.

Preferably, the organic liquid diluent solvent is selected to have an increased solubility of liquid ethylene as hydrocarbon reactant in the organic liquid diluent solvent compared to the solubility of liquid ethylene in propane, at the same temperature and pressure.

The organic liquid diluent solvent may be selected from the group consisting of isobutane, isopentane (2-methylbutane), neopentane (2,2, dimethylpropane), 2-methylpentane, 3-methylpentane, 2,2-dimethylbutane and mixtures of two or more (i.e. mixtures of at least two) thereof.

Preferably, the organic liquid diluent solvent is selected from the group consisting of isobutane, isopentane, neopentane, and mixtures of two or three thereof.

The one or more catalyst solvents may be selected to have an extremely good solubility for components of the catalyst system, must be compatible with the organic liquid diluent solvent and with catalyst and any co-catalyst components of the catalyst system and must be easily separable from the liquid product and from the organic liquid diluent solvent, or it must be a liquid co-monomer product itself.

The catalyst solvent may be selected from the group including, but not necessarily limited to, hydrocarbons such as olefins from C4 to C20, (preferably 1-hexene, 1-octene or C10 to C14 olefin oligomerisation products), norbornene, cyclohexane, methylcyclohexane, methylcyclopentane, methylenecyclopentane, ethylcyclohexane, C5 to C30 linear, branched and cyclic paraffins and polar solvents such as diethyl ether, tetrahydrofuran, acetonitrile, dichloromethane, chloroform, chlorobenzene and the like.

Preferably, the catalyst solvent is selected from the group consisting of 1-hexene, 1-octene, cyclohexane, methylcyclohexane, methylcylopentane, methylenecyclopentane, and mixtures of two or more thereof.

The process may include treating the liquid product to recover unreacted hydrocarbon reactant and organic liquid diluent solvent from the liquid product. This treatment may include at least one distillation stage, typically operating at a lower pressure than the oligomerisation reactor, recovering the hydrocarbon reactant and the organic liquid diluent solvent for recycle to the oligomerisation reactor.

Feeding a hydrocarbon reactant into the oligomerisation reactor may include feeding an excess amount of the hydrocarbon reactant into the oligomerisation reactor.

In the oligomerisation process of the invention, the oligomerisation reaction or reactions are exothermic, requiring a method of cooling of the liquid product or bulk liquid phase in the reactor. The method of cooling or heat removal is dependent on the type of oligomerisation reactor used.

The oligomerisation reactor may be a bubble column reactor, a continuously stirred tank reactor, a loop reactor, a plug flow reactor, or a jet loop reactor. As will be appreciated, when an excess amount of the hydrocarbon reactant is fed into the oligomerisation reactor, evaporation of excess hydrocarbon reactant may remove heat from the liquid product or bulk liquid phase. Similarly, evaporation of organic liquid diluent solvent may remove heat from the liquid product or bulk liquid phase.

The hydrocarbon reactant may be an olefinic feedstock, i.e. comprising one or more olefinic monomers. Preferably, the olefinic feedstock comprises predominantly α-olefins, e.g. ethylene. The ethylene may be fed to the oligomerisation reactor in liquid form.

In one embodiment of the invention, the process uses a catalyst system which favours trimerisation so that the process is predominantly a trimerisation process. In another embodiment of the invention, the process uses a catalyst system which favours tetramerisation so that the process is predominantly a tetramerisation process.

In a further embodiment of the invention, the process uses a catalyst system which favours both trimerisation and tetramerisation so that the process is predominantly both a trimerisation process and a tetramerisation process.

The process is preferably a tetramerisation process so that at least 30% by mass of the liquid product formed is 1-octene. In other words, at least 30% by mass of the products of the oligomerisation reactions taking place, that are in liquid form at the operating temperature and pressure of the oligomerisation reactor, will then be 1-octene. Any products or by products of the oligomerisation reactions that are in gaseous form at the operating temperature and pressure of the oligomerisation reactor, such as ethane, are thus not taken into account.

The process typically includes introducing fresh hydrocarbon reactant or hydrocarbon reactant make-up feed as a vapour. The vapour, e.g. gaseous ethylene, may be condensed before being fed as a liquid to the oligomerisation reactor.

Particularly when the hydrocarbon reactant is ethylene, the oligomerisation reactor may be at an operating pressure of at least about 1 bar(a), more preferably at least about 10 bar(a), most preferably at least about 30 bar(a), e.g. between about 45 bar(a) and about 80 bar(a). The temperature of the oligomerisation reactor may be from about 30° C. to about 120° C., preferably from about 40° C. to about 80° C., e.g. between about 50° C. and about 70° C. These operating conditions are not however necessarily limited to the case where the hydrocarbon reactant is ethylene.

The process may employ at least two oligomerisation reactors, the oligomerisation reactors thus forming a reactor system. Thus, the process may include feeding withdrawn liquid product from a first oligomerisation reactor to a second oligomerisation reactor and feeding fresh hydrocarbon reactant (which may be condensed) also into the second oligomerisation reactor, to form further liquid product. In other words, the process may use at least two oligomerisation reactors in series for the liquid product, with fresh hydrocarbon reactant and, optionally, organic liquid diluent solvent, being fed into each of the oligomerisation reactors (i.e. the oligomerisation reactors are in parallel for the hydrocarbon reactant, but in series for the liquid product).

The at least one catalyst solvent must be introduced into the first oligomerisation reactor; a portion thereof may however also be introduced into the second oligomerisation reactor such that the same constraints as are applied to the first oligomerisation reactor as far as said at least one catalyst solvent and said at least one organic liquid diluent solvent are concerned, are also applied to the second oligomerisation reactor.

The process preferably includes feeding the organic liquid diluent solvent into a bulk liquid phase of the second oligomerisation reactor, such that the mass fraction of the organic liquid diluent solvent in the bulk liquid phase of the second oligomerisation reactor on a hydrocarbon reactant free basis is maintained between about 0.4 and about 0.8, more preferably between about 0.4 and 0.7, most preferably between about 0.45 and 0.6.

The process typically includes treating the withdrawn liquid product to separate co-monomer product and any polymeric by-product from unreacted hydrocarbon reactant and diluent solvent.

Treating the withdrawn liquid product to separate co-monomer product and any polymeric by-product from unreacted hydrocarbon reactant and organic liquid diluent solvent may include flashing the withdrawn liquid product in at least one flash stage. Preferably, the withdrawn liquid product is heated to a temperature of at least 130° C., more preferably at least 155° C., e.g. 167° C., before being flashed in the at least one flash stage.

Preferably, the withdrawn liquid product is flashed at a pressure which is at least 12 bar, more preferably at least 20 bar, e.g. about 30 bar less than the operating pressure of the oligomerisation reactor or reactors.

Treating the withdrawn liquid product to separate co-monomer product and any polymeric by-product from unreacted hydrocarbon reactant and organic liquid diluent solvent may include subjecting an overheads vapour stream from the at least one flash stage to at least one distillation operation and withdrawing the unreacted hydrocarbon reactant and diluent solvent as an overhead stream from the distillation operation.

Advantageously and unexpectedly, with at least 70% by mass of the organic liquid diluent solvent having a normal boiling point below the normal boiling point of 1-hexene, in an ethylene trimerisation or tetramerisation process a single distillation column can be employed to separate the bulk of the organic liquid diluent solvent and unreacted ethylene from the co-monomer product.

The withdrawn unreacted hydrocarbon reactant and organic liquid diluent solvent may be recycled together, i.e. as a single or combined stream, to the oligomerisation reactor.

As will be appreciated, a bottoms stream from the at least one distillation operation will include most of the co-monomer product, e.g. 1-hexene and/or 1-octene, and will include only small amounts of the organic liquid diluent solvent and unreacted hydrocarbon reactant, depending on the separation efficiency of said at least one distillation operation and the boiling point of the organic liquid diluent solvent or the boiling point of each of the organic liquid diluent solvents making up the organic liquid diluent solvent admixture.

The bottoms stream from the at least one distillation operation may be subjected to a product work-up operation which is operated at a lower pressure than said at least one distillation operation. The product work-up operation may produce one or more olefinic product streams, e.g. 1-hexene and/or 1-octene, typically by means of distillation. A vapour purge, including some hydrocarbon reactant, e.g. ethylene, and/or some gaseous by-product or gaseous inerts, e.g. ethane and/or methane, may be produced by the product work-up operation. Advantageously, when substantially all of the organic liquid diluent solvent has a normal boiling point below the normal boiling point of 1-hexene, in an ethylene trimerisation or tetramerisation process, the product work-up section may employ a single distillation column to separate the C6 products from the C8 and higher products, due to the substantial absence of any organic liquid diluent solvent in the bottoms stream from said at least one distillation operation.

Treating the withdrawn liquid product to separate co-monomer product and any polymeric by-product from unreacted hydrocarbon reactant and organic liquid diluent solvent may include subjecting a bottoms stream from said at least one flash stage to at least one further flash stage which is at a lower pressure than said at least one flash stage. Preferably, the bottoms stream from said at least one flash stage is heated to a temperature of at least 190° C., more preferably at least 210° C., e.g. 225° C., before being flashed in said at least one further flash stage.

Preferably, the bottoms stream from said at least one flash stage is flashed in said at least one further flash stage at a pressure which is at least 2 bar, more preferably at least 4 bar, e.g. about 15 bar less than an operating pressure of said at least one flash stage.

Typically, said at least one further flash stage provides a concentrated polymer bottoms stream, which includes most of the polymeric by-product, and an overhead vapour stream which typically includes some unreacted hydrocarbon reactant, some vapourised organic liquid diluent solvent and some co-monomer product. If desired, this overhead vapour stream may be condensed and recycled to the at least one distillation operation where any unreacted hydrocarbon reactant and organic liquid diluent solvent are recovered and recycled to the oligomerisation reactor. Instead, this overhead vapour stream may be fed to the product work-up operation.

In one embodiment of the invention, operating conditions (e.g. temperature and pressure) of the at least one further flash stage are selected such that the overhead vapour stream from the at least one further flash stage is condensed at a pressure of less than 10 bar(a), preferably less than 5 bar(a) with plant cooling water at a temperature of between about 20° C. and about 40° C., such that greater than 95% by mass, preferably greater than 99% by mass of the hydrocarbon reactant reporting to the at least one further flash stage is condensed. The condensed hydrocarbon reactant may then advantageously be recycled to the at least one distillation operation where any unreacted hydrocarbon reactant and organic liquid diluent solvent are recovered and recycled to the oligomerisation reactor.

The oligomerisation reactor may be a bubble column reactor holding said liquid product as part of a bulk liquid phase, in which case feeding a hydrocarbon reactant and organic liquid diluent solvent into the oligomerisation reactor includes feeding into the bulk liquid phase of the bubble column reactor fresh hydrocarbon reactant which has been condensed and said organic liquid diluent solvent and said catalyst system, oligomerising at least a portion of the hydrocarbon reactant in the reactor to form said at least one co-monomer product and polymeric by-product includes allowing at least a portion of the hydrocarbon reactant and the organic liquid diluent solvent to vapourise to form bubbles rising through the bulk liquid phase, with the hydrocarbon reactant oligomerising to form as part of the bulk liquid phase said liquid product which includes organic liquid diluent solvent, said at least one co-monomer product, said catalyst system, unreacted hydrocarbon reactant and said polymeric by-product, and with the evaporation of both the hydrocarbon reactant and the organic liquid diluent solvent effecting heat removal from the bulk liquid phase, and withdrawing liquid product which includes organic liquid diluent solvent, said at least one co-monomer product, said catalyst system, unreacted hydrocarbon reactant and said polymeric by-product from the reactor includes withdrawing some of the bulk liquid phase to maintain the bulk liquid phase at a desired level, the process further including allowing gaseous components comprising any unreacted vapourised hydrocarbon reactant and vapourised organic liquid diluent solvent and any oligomerisation product that reports to a vapour phase to disengage from the bulk liquid phase into a head space in the bubble column reactor above the bulk liquid phase;

withdrawing the gaseous components from the head space;

cooling the gaseous components withdrawn from the head space thereby at least partially to condense the gaseous components, forming a vapour fraction and a liquid fraction both of which include an admixture of unreacted hydrocarbon reactant, organic liquid diluent solvent and oligomerisation product;

recycling the condensed liquid fraction to the bulk liquid phase in the bubble column reactor; and withdrawing the vapour fraction.

In the bubble column reactor, the rising bubbles create turbulence in the bulk liquid phase, thereby also mixing the bulk liquid phase. The liquid or condensed hydrocarbon reactant and the liquid or condensed organic liquid diluent solvent are typically fed at or near a bottom of the bubble column reactor whereas the catalyst system may be introduced into the bubble column reactor in the head space, more preferably in the bulk liquid phase, most preferably near a bottom of the bubble column reactor.

Where a bubble column reactor is chosen as the oligomerisation reactor, the heat removal is at least predominantly effected by means of the latent heat required for evaporation of excess liquid hydrocarbon reactant and the organic liquid diluent solvent. Sufficient (excess) condensed hydrocarbon reactant and organic liquid diluent solvent may be fed and recycled to the bulk liquid phase to balance any reaction exotherm, thereby approaching isothermal behaviour, i.e. maintaining a steady temperature in the bulk liquid phase.

This feature of the invention is important, as the absence of a heat exchanger in direct contact with the bulk liquid phase reduces the surface area that may be susceptible to fouling, which is often a problem with oligomerisation processes, as a result of said formation of polymeric by-product. Furthermore, in one embodiment of the invention, the vigorous mixing caused by the vapourisation of liquid droplets of the hydrocarbon reactant and the organic liquid diluent solvent as they enter the bulk liquid phase to form rising gas bubbles obviates the need for a stirrer or agitator, which may also be susceptible to fouling.

Fresh gaseous hydrocarbon reactant may be combined and condensed with the gaseous components from the head space.

In the case of a bubble column reactor, fresh gaseous hydrocarbon reactant and optionally recycled vapourised unreacted hydrocarbon reactant and optionally recycled vapourised organic liquid diluent solvent recovered from the withdrawn bulk liquid phase is combined and condensed with the gaseous components withdrawn from the head space before the gaseous components are cooled and condensed. A fresh make-up organic liquid diluent solvent stream and/or recycled condensed unreacted hydrocarbon reactant and recycled organic liquid diluent solvent (in liquid form) recovered from the withdrawn bulk liquid phase may similarly be combined with the gaseous components before the gaseous components are cooled and condensed.

Typically however, fresh make-up organic liquid diluent solvent is combined with the liquid fraction, before being fed into the bulk liquid phase. Preferably, in this case, the liquid fraction is sub-cooled. The degree of sub-cooling is preferably sufficient to prevent premature flashing of the liquid fraction in a feed line and/or nozzle used to feed the liquid fraction into the bulk liquid phase.

Preferably, the organic liquid diluent solvent in the bulk liquid phase is selected and maintained at a mass concentration such that, at a reactor pressure of between about 40 bar(a) and about 80 bar(a), preferably between about 40 bar(a) and about 60 bar(a), more preferably between about 45 bar(a) and about 50 bar(a), e.g. about 48 bar(a), more than 99.5% by mass, more preferably more than 99.85% by mass of the gaseous components from the head space, fresh gaseous hydrocarbon reactant, any recycled unreacted hydrocarbon reactant and any recycled organic liquid diluent solvent recovered from the withdrawn bulk liquid phase is condensed at a temperature below 35° C. Preferably, this condensation temperature is between about 4° C. and about 35° C., more preferably between about 10° C. and about 30° C., most preferably between about 12° C. and about 20° C. The temperature of the liquid fraction being fed to the bulk liquid phase in the oligomeric reactor is thus no higher than said condensation temperature.

The temperature of the liquid fraction (i.e. typically an exit temperature of a condenser used to produce the liquid fraction) is therefore lower than the temperature of the bulk liquid phase, providing for an adequate temperature driving force to enable vapourisation of at least a portion of the condensed hydrocarbon reactant and the organic liquid diluent solvent fed into the bulk liquid phase. Surprisingly and advantageously, it is possible to condense more than 99.5% of the gaseous components entering the condenser at temperatures in the order of, say 10° C. to 30° C., at pressures below the supercritical pressure of ethylene, even with hydrogen being present, using an absorption refrigeration system instead of a compression-based refrigeration system. Even more surprisingly and advantageously it is possible to condense more than 99.5% of the gaseous components entering the condenser using a single stage absorption refrigeration system. As will be appreciated, this provides a significant economic benefit to the process of the invention, compared to a process which requires a compression-based refrigeration system.

This is surprising as it was believed that, at pressures below the supercritical pressure of ethylene, the use of a compression-based refrigeration system is unavoidable. The use of a carefully selected organic liquid diluent solvent in the process of the invention, within the correct concentration ranges in the bulk liquid phase, therefore allows substantial reduction in both capital and operating costs of the refrigeration system required for operating a boiling bubble column reactor.

Thus, in the case of a bubble column reactor, the use of an organic liquid diluent solvent as hereinbefore described is particularly important as it facilitates the condensation of the gaseous components before recycling to the bulk liquid phase in order to have the requisite properties for mixing and heat removal in the bubble column reactor. The advantage of increased condensation point temperature of the gaseous components is achieved as the organic liquid diluent solvent has a higher condensation point temperature than does the hydrocarbon reactant. This results in less refrigeration requirements to condense the gaseous components from the head space.

The solubility of the catalyst in the organic liquid diluent solvent is low and hence the use of one or more catalyst solvents, different from the organic liquid diluent solvent and having a higher solubility for the catalyst than the organic liquid diluent solvent, allows feeding of the catalyst system into the bulk liquid phase containing the organic liquid diluent solvent and maintaining the catalyst in solution. The concentration of the catalyst solvent in the liquid product or bulk liquid phase must however be low enough so that it does not adversely affect the concentration of dissolved ethylene in the liquid product or bulk liquid phase as a result of displacement of the organic liquid diluent solvent, in which the ethylene is highly soluble. Hence the requirement for the mass ratio of all organic liquid diluent solvent introduced into the oligomerisation reactor to all catalyst solvent introduced into the oligomerisation reactor over a selected time period being between 15:1 and 4500:1.

Operating the oligomerisation reactor with an organic diluent solvent mass fraction of 0.3 and above in the liquid product or bulk liquid phase provides for an increase in selectivity towards valuable co-monomer product and a corresponding decrease in less valuable secondary incorporation products due to a higher solubility of hydrocarbon reactant in the organic liquid diluent solvent as hereinbefore described and hence allows a higher ratio of hydrocarbon reactant to co-monomer product. Operating the oligomerisation reactor with an organic diluent solvent mass fraction of no more than 0.8 in the liquid product or bulk liquid phase reduces the flow rates of organic liquid diluent solvent and hydrocarbon reactant that must be recycled. As can be appreciated, this reduces the capital and operating costs involved in recycling these components.

In addition, operating the oligomerisation reactor with an organic diluent solvent mass fraction of no more than 0.8 in the liquid product or bulk liquid phase reduces the likelihood of catalyst, which has been shown to be sparingly soluble in the organic liquid diluent solvent, coming out of solution.

In one embodiment of the invention, the process is a broad range ethylene oligomerisation process, employing a catalyst system and yielding a Schulz Flory or Poisson distribution of olefins. The olefins from this process find application as feedstock for detergents, plasticiser alcohols, linear alkyl benzenes and as co-monomers for the production of polyethylene. Non-limiting examples of such catalyst systems are nickel based systems bearing α-diimine ligands and activated by a dialkyl aluminium halide cocatalyst (e.g. as described in WO 0010945), or nickel based systems having chelating ligands such as 2-diphenyl phosphine benzoic acid in combination with a borohydride reducing agent (e.g. as described in U.S. Pat. No. 3,676,523). Also possible is the use of trialkylaluminium catalysts for the production of a broad range of alpha olefins.

In a further embodiment of the invention, the process is predominantly a trimerisation of ethylene process. The trimerisation of ethylene to 1-hexene is a significant commercial operation. In addition to its use as a specific chemical, 1-hexene is extensively used in polymerisation processes either as a monomer or co-monomer. Non-limiting examples of ethylene trimerisation catalyst systems are provided in a review by Dixon, J. T., Green, M. J., Hess, F. M., and Morgan, D. H., Journal of Organometallic Chemistry, 2004, 689, 3641-3668. A few examples include the Phillips Cr/pyrollide/TEA system, the Dutch Polymer Institute Ti/benzyl substituted Cp/MAO system, the BP Cr/o-methoxyphenylPNP/MAO system and the Sasol Cr/SNS/MAO and Cr/o-alkylphenylPNP/MAO systems. Examples of ligand-free, tantalum-based catalyst systems have also been reported by Arteaga-Muller, R, Tsurugi, H., Saito, T, Yanagawa, M, Oda, S. and Mashima, K., J.A.C.S Communications, 2009, 131, 5370-5371.

In another embodiment of the invention, the process is predominantly a tetramerisation of ethylene process. As in the case of 1-hexene described above, 1-octene is also used as a co-monomer in the production of linear low density polyethylene. Non-limiting examples of selective ethylene tetramerisation catalyst systems include the ubiquitous Cr/PNP/MAO systems, beginning with PNP ligands containing no substituents on the phenyl rings attached to the P-atoms (e.g. as described in WO 2004/056479) and those with p-methoxy groups on the phenyl rings (e.g. as described in WO 2004/056480). In addition to this, PNP systems containing o-fluoro groups on the phenyl rings are described in US2008/0242811, and PNP systems bearing pendant donor atoms on the nitrogen linker are described in WO 2007/088329. Multi-site PNP ligands are discussed in US 2008/0027188.

In addition to the Cr/PNP systems, chromium systems bearing N, N-bidentate ligands (e.g. as described in US 2006/0247399) as well as systems containing PPN ligands (e.g. as described in WO 2008/077911 and WO 2008/077908) can be used. PNPNH as well as PNPNP ligands are described in WO 2009/006979. Finally, chromium/PCCP/MAO systems are described in WO 2008/088178 and WO 2009/022770.

In a further embodiment, the process in accordance with the invention is predominantly both a trimerisation process and a tetramerisation process. In yet a further embodiment, the process in accordance with the second aspect of the invention is a tetramerisation of ethylene process in combination with a trimerisation of ethylene process, or broad range oligomerisation of ethylene process, as described in WO 2005/123884. The process may be a combination of a tetramerisation of ethylene and trimerisation of ethylene process as described in WO 2005/123884, WO 2007/057455 and WO 2006/108803. The process may also be a tandem oligomerisation/polymerisation process as discussed in WO 2004/056480.

As indicated hereinbefore, in one embodiment of the invention, the process is preferably a tetramerisation process producing at least 30% 1-octene.

In one embodiment of the invention, the catalyst is a dissolved transition metal compound catalyst, e.g. a chromium catalyst, with a heteroatomic or homoatomic, ligand, typically used with an activator. A number of dissolved transition metal compound catalysts have been developed for use to trimerise or tetramerise olefins, e.g. as disclosed in U.S. Pat. No. 4,668,838; EP 0668105; U.S. Pat. No. 5,750,817; U.S. Pat. No. 6,031,145; U.S. Pat. No. 5,811,618; WO 03/053890; WO 2004/056478; WO 2004/056477; WO 2004/056479; WO 2004/056480; WO 2005/123633 and WO 2007/007272.

Some of these catalysts are selective for $C_6$ and $C_8$ oligomeric products, e.g. 1-hexene and 1-octene, and the Applicant believes that such catalysts will be particularly advantageous for use with the process according to the second aspect of the invention as the selective production of 1-hexene and 1-octene from ethylene is commercially important.

In a preferred embodiment of the process in accordance with the invention the catalyst also includes one or more activators. Such an activator may be a compound that generates an active catalyst when the activator is combined with a source of transition metal and a ligating compound.

Suitable activators include organoaluminium compounds, boron compounds including those disclosed in WO 2010/092554 and WO 2011/048527, aluminate activators including those disclosed in WO 2008/038173 and WO2007/039851 e.g. trityl perfluoro-tributyl aluminate, and the like. Such activators may optionally be used in combination with alkylaluminium or alkylzinc compounds.

Suitable organoaluminium compounds include compounds of the formula $Al(R^1)_3$ ($R^1$ being the same or different), where each $R^1$ is independently a $C_1$-$C_{12}$ alkyl, an oxygen containing moiety or a halide, aluminoxanes, and compounds such as $LiAlH_4$ and the like. Aluminoxanes are well known in the art as typically oligomeric compounds which can be prepared by the controlled addition of water to an alkylaluminium compound, for example trimethylaluminium. In such process the alkylaluminium compounds are only partially hydrolysed to prevent or at least to reduce the formation of aluminium hydroxide during the preparation of aluminoxanes. Commercially available aluminoxanes consequently include unreacted alkylaluminium. The result is that commercially available aluminoxanes are usually mixtures of an aluminoxane and an alkylaluminium. Such compounds can be linear, cyclic, cages or mixtures thereof. Examples of suitable aluminium compounds in the form of organoaluminium activators include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, $[Ph_3C][Al\{OC(CF_3)_3\}]$, methylaluminoxane (MAO), ethylaluminoxane (EAO), isobutylaluminoxane (iBuAO), modified alkylaluminoxanes such as modified methylaluminoxane (MMAO) and mixtures of the above-mentioned compounds.

In this specification the term "aluminoxanes" is used to denote a compound represented by the general formulae $(R^a—Al—O)_n$ and $R^b(R^c—Al—O)_n—AlR^d_2$ wherein $R^a$, $R^b$, $R^c$, and $R^d$ are independently a $C_1$-$C_{30}$ alkyl or haloalkyl radical, for example methyl, ethyl, propyl, butyl, 2-methyl-propyl, pentyl, isopentyl, neopentyl, cyclopentyl, hexyl, isohexyl, cyclohexyl, heptyl, octyl, iso-octyl, 2-ethylhexyl, decyl, 2-phenyl-propyl, 2-(4-fluorophenyl)-propyl, 2,3-dimethyl-butyl, 2,4,4-trimethyl-pentyl and dodecyl; and n has the value of 2 to 50. Preferably n is at least 4.

Particularly favoured aluminoxane products are methylaluminoxane and modified methylaluminoxane. Modified methylaluminoxane is a methyluminonoxane product which contains a proportion of longer alkyl chain modifiers.

Examples of suitable organoboron compounds are boroxines, $NaBH_4$, triethylborane, tris(pentafluorophenyl)borane, trityl tetrakis(pentafluorophenyl)borate, dimethylanilinium tetrakis(pentafluorophenyl)borate, tributyl borate, dialkylmethylammonium tetrakis(pentafluorophenyl)borate, where alkyl=$C_2$ to $C_{22}$, trialkylammonium tetrakis(pentafluorophenyl)borate, where alkyl=C2 to C22 and the like. These boron containing compounds may be used in conjunction with the $Al(R^1)_3$ compounds discussed above.

The activator may also be or contain a compound that acts as a reducing or oxidising agent, such as sodium or zinc metal and the like, or hydrogen or oxygen and the like.

The activator may be selected from alkylaluminoxanes such as methylaluminoxane (MAO), high stability methylaluminoxane (MAO HS), ethylaluminoxane (EAO), isobutylaluminoxane (iBuAO) as well as modified alkylaluminoxanes such as modified methylaluminoxane (MMAO).

The transition metal source and the aluminoxane may be combined in proportions to provide Al/transition metal molar ratios from about 1:1 to 10 000:1, preferably from about 1:1 to 1000:1, and more preferably from 1:1 to 500:1.

The process in accordance with the invention may include the step of adding to the catalyst system a trialkylaluminium compound in amounts of between 0.01 to 1000 mol per mol of alkylaluminoxane.

In one embodiment of the invention the oligomerisation catalyst includes a combination of
i) a source of Cr; and
ii) a ligating compound of the formula

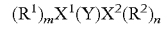

wherein: $X^1$ and $X^2$ are independently selected from the group consisting of N, P, As, Sb, Bi, 0, S and Se; preferably P and N, most preferably P Y is a linking group between $X^1$ and $X^2$; preferably consisting of —N(R)—, —N(R)—N(R')—, —C(R)(R')—N(R")— or a hydrocarbylene group, where R, R' and R" are H, hydrocarbyl or heterohydrocarbyl groups, preferably hydrocarbyl or heterohydrocarbyl;

m and n are independently 0, 1 or a larger integer, preferably both m and n are 2; and $R^1$ and $R^2$ are independently hydrogen, a hydrocarbyl group or a heterohydrocarbyl group, and $R^1$ being the same or different when m>1, and $R^2$ being the same or different when n>1.

In this specification the following definitions apply:

A "hydrocarbyl group" as per IUPAC is a univalent group formed by removing one hydrogen atom from a hydrocarbon.

A "hydrocarbylene group" as per IUPAC is a divalent group formed by removing two hydrogen atoms from a hydrocarbon, the free valencies of which are not engaged in a double bond.

A "heterohydrocarbyl group" is a univalent group formed by removing one hydrogen atom from a carbon atom of a heterohydrocarbon, that is a hydrocarbon compound which includes at least one heteroatom (that is not being H or C), and which group covalently bonds with one other moiety through the resultant free valency on that carbon atom.

Most preferably the ligating compound is of the formula

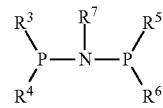

with $R^3$ to $R^6$ as defined above and $R^7$ is a hydrocarbyl or heterohydrocarbyl group.

Preferably each of $R^3$ to $R^6$ is an alkyl (preferably methyl, ethyl or isopropyl) or aromatic (preferably phenyl or substituted phenyl).

Most preferably $R^3$ to $R^6$ is a substituted phenyl.

Non limiting examples of the ligating compound are: (phenyl)$_2$PN(methyl)P(phenyl)$_2$; (phenyl)$_2$PN(ethyl)P(phenyl)$_2$; (phenyl)$_2$PN(propyl)P(phenyl)$_2$; (phenyl)$_2$PN(butyl)P (phenyl)$_2$; (phenyl)$_2$PN(pentyl)P(phenyl)$_2$; (phenyl)$_2$PN (hexyl)P(phenyl)$_2$; (phenyl)$_2$PN(heptyl)P(phenyl)$_2$; (phenyl)$_2$PN(octyl)P(phenyl)$_2$; (phenyl)$_2$PN(nonyl)P(phenyl)₂; (phenyl)₂PN(decyl)P(phenyl)₂; (phenyl)₂PN(cyclopropyl)P(phenyl)₂; (phenyl)₂PN(cyclobutyl)P(phenyl)₂; (phenyl)₂PN(cyclopentyl)P(phenyl)₂; (phenyl)₂PN(cyclohexyl)P(phenyl)₂; (phenyl)₂PN(cycloheptyl)P(phenyl)₂; (phenyl)₂PN(cyclooctyl)P(phenyl)₂; (phenyl)₂PN(cyclodecyl)P(phenyl)₂; (phenyl)₂PN(cyclododecyl)P(phenyl)₂; (phenyl)₂PN(isopropyl)P(phenyl)₂; (phenyl)₂PN(isobutyl)P(phenyl)₂; (phenyl)₂PN(secbutyl)P(phenyl)₂; (phenyl)₂PN(tertiarybutyl)P(phenyl)₂; (phenyl)₂PN(neopentyl)P(phenyl)₂; (phenyl)₂PN(1,2-dimethyl-propyl)P(phenyl)₂; (phenyl)₂PN(allyl)P(phenyl)₂; (phenyl)₂PN(methylheptyl)P(phenyl)₂; (phenyl)₂PN(1,5-dimethyl-heptyl)P(phenyl)₂; (phenyl)₂PN(2-ethylhexyl)P(phenyl)₂; (phenyl)₂PN(adamantyl)P(phenyl)₂; (phenyl)₂PN(adamantylmethyl)P(phenyl)₂; (phenyl)₂PN(3-trimethoxysilane-propyl)P(phenyl)₂; (phenyl)₂PN(indanyl)P(phenyl)₂; (phenyl)₂PN(cyclohexylethyl)P(phenyl)₂; (phenyl)₂PN(2-methylcyclohexyl)P(phenyl)₂; (phenyl)₂PN(cyclohexanemethyl)P(phenyl)₂; (phenyl)₂PN(benzyl)P(phenyl)₂; (phenyl)₂PN(phenyl)P(phenyl)₂; (phenyl)₂PN((4-methoxy)-phenyl)P(phenyl)₂; (phenyl)₂PN((3-methoxy)-phenyl)P(phenyl)₂; (phenyl)₂PN((2-methoxy)phenyl)P(phenyl)₂; (phenyl)₂PN((4-t-butyl)phenyl)P(phenyl)₂; (phenyl)₂PN((4-nitro)-phenyl)P(phenyl)₂; (phenyl)₂PN(1-naphthyl)P(phenyl)₂; (phenyl)₂PN(2-naphthyl)P(phenyl)₂; (phenyl)₂PN(4-pyridyl)P(phenyl)₂ (phenyl)₂PN(3-(N-morpholine)propyl)P(phenyl)₂; (phenyl)₂PN(2-naphtyl-ethyl)P(phenyl)₂; (phenyl)₂PN(1-naphtylmethyl)P(phenyl)₂; (phenyl)₂PN(diphenylmethyl)P(phenyl)₂; (phenyl)₂PN(1,2-diphenylethyl)P(phenyl)₂; (phenyl)₂PN(phenylethyl)P(phenyl)₂; (phenyl)₂PN((2-methyl)phenyl)P(phenyl)₂; (phenyl)₂PN((3-methyl)phenyl)P(phenyl)₂; (phenyl)₂PN((4-methyl)phenyl)P(phenyl)₂; (phenyl)₂PN((2,6-dimethyl)phenyl)P(phenyl)₂; (phenyl)₂PN((2-ethyl)-phenyl)P(phenyl)₂; (phenyl)₂PN(1,2,3,4-Tetrahydronaphthyl)P(phenyl)₂; (phenyl)₂PN((2-methyl)cyclohexyl)P(phenyl)₂; (phenyl)₂PN((3-methyl)cyclohexyl)P(phenyl)₂; (phenyl)₂PN((4-methyl)cyclohexyl)P(phenyl)₂; (phenyl)₂PN((2-ethyl)cyclohexyl)P(phenyl)₂; (phenyl)₂PN((2-isopropyl)cyclohexyl)P(phenyl)₂; (phenyl)₂PN((2,6-dimethyl)cyclohexyl)P(phenyl)₂; (phenyl)₂PN(exo-2-norbornanyl)P(phenyl)₂; (phenyl)₂PN(isopinocampheyl)P(phenyl)₂; (phenyl)₂PN(dimethylamino)P(phenyl)₂; (phenyl)₂PN(phthalimido)P(phenyl)₂; (phenyl)₂PN(pyrrolyl)P(phenyl)₂; (phenyl)₂PN(trimethylsiyl)P(phenyl)₂; (phenyl)₂PN(dimethyltertiarybutylsilyl)P(phenyl)₂; [(phenyl)₂P]₂N(1,1'-bis(cyclohexyl)-4,4'-methylene))N[P(phenyl)₂]₂; ([(phenyl)₂P]₂N(1,6-hexylene-)N[P(phenyl)₂]₂; (2,2',2''-triethylamino)[N[P(phenyl)₂]₂]₃; (4-biphenyl)PN(methyl)P(4-biphenyl)₂; (2-naphthyl)₂PN(methyl)P(2-naphthyl)₂; (4-methylphenyl)₂PN(methyl)P(4-methylphenyl)₂; (3-methylphenyl)₂PN(methyl)P(3-methylphenyl)₂; (2-naphthyl)₂PN(methyl)P(phenyl)₂; (2-naphthyl)(phenyl)PN(methyl)P(2-naphthyl)(phenyl); (2-naphthyl)₂PN(methyl)P(2-naphthyl)(phenyl); (2-naphthyl)(phenyl)PN(methyl)P(phenyl)₂; (2-methylphenyl)₂PN(methyl)P(2-methylphenyl)₂; (2-ethylphenyl)₂PN(methyl)P(2-ethylphenyl)₂; (2-isopropylphenyl)₂PN(methyl)P(2-isopropylphenyl)₂; (2-methylphenyl)₂PN(ethyl)P(2-methylphenyl)₂; (2-methylphenyl)₂PN(methyl)P(2-methylphenyl)(phenyl); (2-methylphenyl)(phenyl)PN(isopropyl)P(2-methyl phenyl)(phenyl); (2-methylphenyl)₂PN(methyl)P(phenyl)₂; (2-methylphenyl)(phenyl)PN(isopropyl)P(phenyl)₂; (ethyl)₂PN(methyl)P(ethyl)₂; (ethyl)₂PN(isopropyl)P(ethyl)₂; (ethyl)₂PN(tertiarybutyl)P(ethyl)₂; (methyl)₂PN(isopropyl)P(methyl)₂; (isopropyl)₂PN(methyl)P(isopropyl)₂; (ethyl)₂PN(isopropyl)P(ethyl)(phenyl); (ethyl)(phenyl)PN(isopropyl)P(ethyl)(phenyl); (ethyl)₂PN(isopropyl)P(phenyl)₂; (ethyl)(phenyl)PN(isopropyl)P(phenyl)₂; (2-thiophenyl)₂PN(isopropyl)P(2-thiophenyl)₂; (diphenylphosphonite)N(isopropyl)(diphenylphosphonite); (dibenzothiaphosphonine)N(isopropyl)(dibenzothiaphosphonine); (dibenzooxaphosphonine)N(isopropyl)(dibenzooxaphosphonine); (phenyl)₂PN(methyl)N(methyl)P(phenyl)₂; (phenyl)₂PN(ethyl)N(ethyl)P(phenyl)₂; (phenyl)₂PN(phenyl)N(phenyl)P(phenyl)₂; (phenyl)₂PN(isopropyl)N(isopropyl)P(phenyl)₂; (phenyl)₂PN(isopropyl)N(methyl)P(phenyl)₂; (phenyl)₂PN(isopropyl)N(methyl)P(phenyl)₂; (4-methylphenyl)₂P—N(CH₃)N(CH₃)—P(4-methylphenyl)₂; (3-methylphenyl)₂P—N(CH₃)N(CH₃)—P(3-methylphenyl)₂; (2-methylphenyl)₂P—N(CH₃)N(CH₃)—P(2-methylphenyl)₂; (2-ethylphenyl)₂P—N(CH₃)N(CH₃)—P(2-ethylphenyl)₂; (2-isopropylphenyl)₂P—N(CH₃)N(CH₃)—P(2-isopropylphenyl)₂; (2-methylphenyl)₂P—N(CH₃)N(CH₃)—P(2-methylphenyl)(phenyl); (2-methylphenyl)₂P—N(CH₃)N(CH₃)—P(phenyl)₂; (ethyl)₂P—N(CH₃)N(CH₃)—P(ethyl)₂; (methyl)₂P—N(CH₃)N(CH₃)—P(methyl)₂; (isopropyl)₂P—N(CH₃)N(CH₃)—P(isopropyl)₂; (ethyl)₂P—N(CH₃)N(CH₃)—P(ethyl)(phenyl); (ethyl)(phenyl)P—N(CH₃)N(CH₃)—P(ethyl)(phenyl); (ethyl)₂P—N(CH₃)N(CH₃)—P(phenyl)₂; (ethyl)(phenyl)P—N(CH₃)N(CH₃)—P(phenyl)₂; (2-thiophenyl)₂P—N(CH₃)N(CH₃)—P(2-thiophenyl)₂; (2-naphthyl)₂P—N(CH₃)N(CH₃)—P(2-naphthyl)₂; (4-biphenyl)₂P—N(CH₃)N(CH₃)—P(4-biphenyl)₂; (phenyl)₂P-1,8-naphthyl-P(phenyl)₂; (phenyl)₂P-9,10-phenanthrene-P(phenyl)₂; (phenyl)₂P-4,5-phenanthrene-P(phenyl)₂; (phenyl)₂P—C(CH₃)₂—P(phenyl)₂; (phenyl)₂P—C(CH₂)₂—P(phenyl)₂; (phenyl)₂P-1,2-benzene-P(phenyl)₂; (4-methylphenyl)₂P-1,2-benzene-P(4-methylphenyl)₂; (3-methylphenyl)₂P-1,2-benzene-P(3-methylphenyl)₂; (2-methylphenyl)₂P-1,2-benzene-P(2-methylphenyl)₂; (2-ethylphenyl)₂P-1,2-benzene-P(2-ethylphenyl)₂; (2-isopropylphenyl)₂P-1,2-benzene-P(2-isopropylphenyl)₂; (2-methylphenyl)₂P-1,2-benzene-P(2-methylphenyl)(phenyl); (2-methylphenyl)₂P-1,2-benzene-P(phenyl)₂; (ethyl)₂P-1,2-benzene-P(ethyl)₂; (methyl)₂P-1,2-benzene-P(methyl)₂; (isopropyl)₂P-1,2-benzene-P(isopropyl)₂; (ethyl)₂P-1,2-benzene-P(ethyl)(phenyl); (ethyl)(phenyl)P-1,2-benzene-P(ethyl)(phenyl); (ethyl)₂P-1,2-benzene-P(phenyl)₂; (ethyl)(phenyl)P-1,2-benzene-P(phenyl)₂; (2-thiophenyl)₂P-1,2-benzene-P(2-thiophenyl)₂; (2-naphthyl)₂P-1,2-benzene-P(2-naphthyl)₂; (4-biphenyl)₂P-1,2-benzene-P(4-biphenyl)₂; (phenyl)₂P—CH2CH2-P(phenyl)₂; (4-methylphenyl)₂P—CH₂CH₂—P(4-methylphenyl)₂; (3-methylphenyl)₂P—CH₂CH₂—P(3-methylphenyl)₂; (4-methylphenyl)₂P—CH₂CH₂—P(4-methylphenyl)(phenyl); (4-methylphenyl)(phenyl)P—CH₂CH₂—P(4-methylphenyl)(phenyl); (4-methylphenyl)₂P—CH₂CH₂—P(phenyl)₂; (4-methyl phenyl)(phenyl)P—CH₂CH₂—P(phenyl)₂; (2-methylphenyl)₂P—CH₂CH₂—P(2-methylphenyl)₂; (2-ethylphenyl)₂P—CH₂CH₂—P(2-ethylphenyl)₂; (2-isopropylphenyl)₂P—CH₂CH₂—P(2-isopropylphenyl)₂; (2-methylphenyl)₂P—CH₂CH₂—P(2-methylphenyl)(phenyl); (2-methlylphenyl)₂P—CH₂CH₂—P(phenyl)₂; (ethyl)₂P—CH₂CH₂—P(ethyl)₂; (methyl)₂P—CH₂CH₂—P(methyl)₂; (isopropyl)₂P—CH₂CH₂—P(isopropyl)₂; (ethyl)₂P—CH₂CH₂—P(ethyl)(phenyl); (ethyl)(phenyl)P—CH2CH₂—P(ethyl)(phenyl); (ethyl)₂P—CH₂CH₂—P(phenyl)₂; (ethyl)(phenyl)P—CH₂CH₂—P(phenyl)₂; (2-thiophenyl)₂P—CH₂CH₂—P(2-thiophenyl)₂; (phenyl)₂PB(phenyl)P(phenyl)₂; (phenyl)₂PP(phenyl)P(phenyl)₂; (phenyl)₂PSi(methyl)₂P(phenyl)₂; (phenyl)₂AsN(isopropyl)As(phenyl)₂; (phenyl)SN(isopropyl)S(phenyl); (phenyl)₂PN(isopropyl)S(phenyl); (phenyl)₂PN(isopropyl)

As(phenyl)₂; (phenyl)₂PN(isopropyl)P(=O)(phenyl)₂; (phenyl)₂P(=O)N(isopropyl)P(=O)(phenyl)₂; (phenyl)₂PN(isopropyl)P(=S)(phenyl)₂; (phenyl)₂P(=S)N(isopropyl)P(=S)(phenyl)₂; (phenyl)₂P(=O)N(isopropyl)P(=S) (phenyl)₂; (4-trifluoromethylphenyl)₂PN(isopropyl)P(4-trifluoromethylphenyl)₂; (4-chlorophenyl)₂PN(isopropyl)P(4-chlorophenyl)₂; (4-methoxyphenyl)₂PN(methyl)P(4-methoxyphenyl)₂; (4-methoxyphenyl)₂PN(isopropyl)P(4-methoxyphenyl)₂; (3-methoxyphenyl)₂PN(methyl)P(3-methoxyphenyl)₂; (4-methoxyphenyl)₂PN(isopropyl)P(4-methoxyphenyl)(phenyl); (4-methoxyphenyl)(phenyl)PN(isopropyl)P(4-methoxyphenyl)(phenyl); (4-methoxyphenyl)₂PN(isopropyl)P(phenyl)₂; (4-methoxyphenyl)(phenyl)PN(isopropyl)P(phenyl)₂; (4-methoxyphenyl)₂P—N(CH₃)N(CH₃)—P(4-methoxyphenyl)₂; (3-methoxyphenyl)₂P—N(CH₃)N(CH₃)—P(3-methoxyphenyl)₂; (4-methoxyphenyl)₂P—N(CH₃)N(CH₃)—P(4-methoxyphenyl)(phenyl); (4-methoxyphenyl)(phenyl)P—N(CH₃)N(CH₃)—P(4-methoxyphenyl)(phenyl); (4-methoxyphenyl)₂P—N(CH₃)N(CH₃)—P(phenyl)₂; (4-methoxyphenyl)(phenyl)P—N(CH₃)N(CH₃)—P(phenyl)₂; (4-methoxyphenyl)₂P-1,2-benzene-P(4-methoxyphenyl)₂; (3-methoxyphenyl)₂P-1,2-benzene-P(3-methoxyphenyl)₂; (4-methoxyphenyl)₂P-1,2-benzene-P(4-methoxyphenyl)(phenyl); (4-methoxyphenyl)(phenyl)P-1,2-benzene-P(4-methoxyphenyl)(phenyl); (4-methoxyphenyl)₂P-1,2-benzene-P(phenyl)₂; (4-methoxyphenyl)(phenyl)P-1,2-benzene-P(phenyl)₂; (3-methoxyphenyl)₂P(CH₂CH₂)P(3-methoxyphenyl)₂; (3-methoxyphenyl)₂P(CH₂CH₂)P(3-methoxyphenyl)(phenyl); (3-methoxyphenyl)(phenyl)P(CH₂CH₂CH₂)P(3-methoxyphenyl)(phenyl); (3-methoxyphenyl)(phenyl)P(CH₂CH₂)P(3-methoxyphenyl)(phenyl); (3-methoxyphenyl)(phenyl)P(CH₂)P(3-methoxyphenyl)(phenyl); (3-methloxyphenyl)₂P(CH₂CH₂)P(phenyl)₂; (3-methoxyphenyl)(phenyl)P(CH₂CH₂)P(phenyl)₂; (4-methoxyphenyl)₂P(CH₂CH₂)P(4-methoxyphenyl)₂; (4-methoxyphenyl)₂P(CH₂CH₂)P(4-methoxyphenyl)(phenyl); (4-methoxyphenyl)(phenyl)P(CH₂CH₂CH₂)P(4-methoxyphenyl)(phenyl); (4-methoxyphenyl)(phenyl)P(CH₂CH₂)P(4-methoxyphenyl)(phenyl); (4-methoxyphenyl)(phenyl)P(CH₂)P(4-methoxyphenyl)(phenyl); (4-methoxyphenyl)₂P(CH₂CH₂)P(phenyl)₂; (4-methoxyphenyl)(phenyl)P(CH₂CH₂)P(phenyl)₂; (2-methoxyphenyl)₂PN(methyl)P(2-methoxyphenyl)₂; (2-methoxyphenyl)₂PN(ethyl)P(2-methoxyphenyl)₂; (2-methoxyphenyl)₂PN(phenyl)P(2-methoxyphenyl)₂; (2-methoxyphenyl)₂PN(methyl)N(methyl)P(2-methoxyphenyl)₂; (2-methoxyphenyl)₂P(CH₂)P(2-methoxyphenyl)₂; (2-methoxyphenyl)₂P(CH₂CH₂)P(2-methoxyphenyl)₂; tri(2-methoxyphenyl)phosphane; tri(2-methoxymethoxyphenyl)phosphane; (2-methoxyphenyl)₂PN(isopropyl)P(2-methoxyphenyl)(phenyl); (2-methoxyphenyl)(phenyl)PN(isopropyl)P(2-methoxyphenyl)(phenyl); (2-methoxyphenyl)₂PN(isopropyl)P(phenyl)₂; (2-methoxyphenyl)(phenyl)PN(isopropyl)P(phenyl)₂; (2-methoxyphenyl)₂PN(methyl)P(2-methoxyphenyl)(phenyl); (2-methoxyphenyl)(phenyl)PN(methyl)P(2-methoxyphenyl)(phenyl); (2-methoxyphenyl)₂PN(methyl)P(phenyl)₂; (2-methoxyphenyl)(phenyl)PN(methyl)P(phenyl)₂; (2-ethoxyphenyl)₂PN(methyl)P(2-ethoxyphenyl)₂; (2-isopropoxyphenyl)₂PN(methyl)P(2-isopropoxyphenyl)₂; (2-hydroxyphenyl)₂PN(methyl)P(2-hydroxyphenyl)₂; (2-nitrophenyl)₂PN(methyl)P(2-nitrophenyl)₂; (2-(dimethylamino)phenyl)₂PN(methyl)P(2-(dimethylamino)phenyl)₂; (2,3-dimethoxyphenyl)₂PN(methyl)P(2,3-dimethoxyphenyl)₂; (2,4-dimethoxyphenyl)₂PN(methyl)P(2,4-dimethoxyphenyl)₂; (2,6-dimethoxyphenyl)₂PN(methyl)P(2,6-dimethoxyphenyl)₂; (2,4,6-trimethoxyphenyl)₂PN(methyl)P(2,4,6-tri-methoxyphenyl)₂; (2-methoxyphenyl)(2-methylphenyl)PN(methyl)P(2-methylphenyl)₂; (2-methoxymethoxyphenyl)₂PN(methyl)P(2-methoxymethoxyphenyl)₂; (2-methoxyphenyl)₂PN(methyl)P(2-methoxyphenyl)(phenyl); (2-methoxyphenyl)(phenyl)PN(methyl)P(2-methoxyphenyl)(phenyl); (2-methoxyphenyl)₂PN(methyl)P(phenyl)₂; (2-methoxyphenyl)(phenyl)PN(methyl)P(phenyl)₂; (2-methoxyphenyl)₂P—N(CH₃)N(CH₃)—P(2-methoxyphenyl)₂; (2-methoxyphenyl)₂P-1,2-benzene-P(2-methoxyphenyl)₂; (2-methoxyphenyl)₂P(CH₂CH₂)P(2-methoxyphenyl)₂; (2-methoxyphenyl)₂P(CH₂CH₂)P(2-methoxyphenyl)(phenyl); (2-methoxyphenyl)(phenyl)P(CH₂CH₂CH₂)P(2-methoxyphenyl)(phenyl); (2-methoxyphenyl)(phenyl)P(CH₂CH₂)P(2-methoxyphenyl)(phenyl); (2-methoxyphenyl)(phenyl)P(CH₂)P(2-methoxyphenyl)(phenyl); (2-methoxyphenyl)₂P(CH₂CH₂)P(phenyl)₂; (2-methoxyphenyl)(phenyl)P(CH₂CH₂)P(phenyl)₂; (2-ethoxyphenyl)₂P(CH₂CH₂)P(2-ethoxyphenyl)₂; (2-ethoxyphenyl)₂P(CH₂CH₂)P(2-ethoxyphenyl)(phenyl); (2-ethoxyphenyl)(phenyl)P(CH₂CH₂CH₂)P(2-ethoxyphenyl)(phenyl); (2-ethoxyphenyl)(phenyl)P(CH₂CH₂)P(2-ethoxyphenyl)(phenyl); (2-ethoxyphenyl)(phenyl)P(CH₂)P(2-ethoxyphenyl)(phenyl); (2-ethoxyphenyl)₂P(CH₂CH₂)P(phenyl)₂; (2-ethoxyphenyl)(phenyl)P(CH₂CH₂)P(phenyl)₂; (2-isopropoxyphenyl)₂P(CH₂CH₂)P(2-isopropoxyphenyl)₂; (2-isopropoxyphenyl)₂P(CH₂CH₂)P(2-isopropoxyphenyl)(phenyl); (2-isopropoxyphenyl)(phenyl)P(CH₂CH₂CH₂)P(2-isopropoxyphenyl)(phenyl); (2-isopropoxyphenyl)(phenyl)P(CH₂CH₂)P(2-isopropoxyphenyl)(phenyl); (2-isopropoxyphenyl)(phenyl)P(CH₂)P(2-isopropoxyphenyl)(phenyl); (2-isopropoxyphenyl)₂P(CH₂CH₂)P(phenyl)₂; (2-isopropoxyphenyl)(phenyl)P(CH₂CH₂)P(phenyl)₂; (phenyl)₂PCH₂CH₂NHCH₂CH₂P(phenyl)₂; (ethyl)₂PCH₂CH₂NHCH₂CH₂P(ethyl)₂; (phenyl)₂PCH₂CH₂NHCH₂CH₂P(ethyl)₂; (phenyl)(ethyl)PCH₂CH₂NHCH₂CH₂P(phenyl)₂; (phenyl)SCH₂CH₂NHCH₂CH₂S(phenyl); (ethyl)₂PCH₂CH₂NHCH₂CH₂P(ethyl)₂; (decyl)₂PCH₂CH₂NHCH₂CH₂P(decyl)₂; (phenyl)₂PCH₂CH₂NHCH₂CH₂S(ethyl); (phenyl)₂PCH₂CH₂P(phenyl)CH₂CH₂P(phenyl)₂ and (phenyl)₂PCH₂CH₂CH₂NHCH₂CH₂P(phenyl)₂. (2-fluorophenyl)₂PN(isopropyl)P(2-fluorophenyl)₂, Ph₂PN(Me)P(2-methoxyphenyl)₂, (phenyl)₂PN(isopropyl)P(phenyl)NH(isopropyl), (phenyl)₂PN(isopropyl)P(phenyl)N(phenyl)H, (phenyl)₂PN(isopropyl)P(phenyl)N(t-butyl)H, (phenyl)₂PN(isopropyl)P(phenyl)N(CH(CH₃)(phenyl))H, (phenyl)₂PN(CH₂)(2-methoxyphenyl)P(phenyl)₂, (phenyl)₂PN(CH₂)₂(2-methoxyphenyl)P(phenyl)₂, (phenyl)₂PN(CH₂)₃(2-methoxyphenyl)P(phenyl)₂,

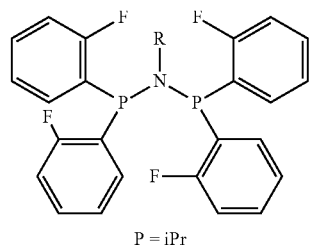

P = iPr

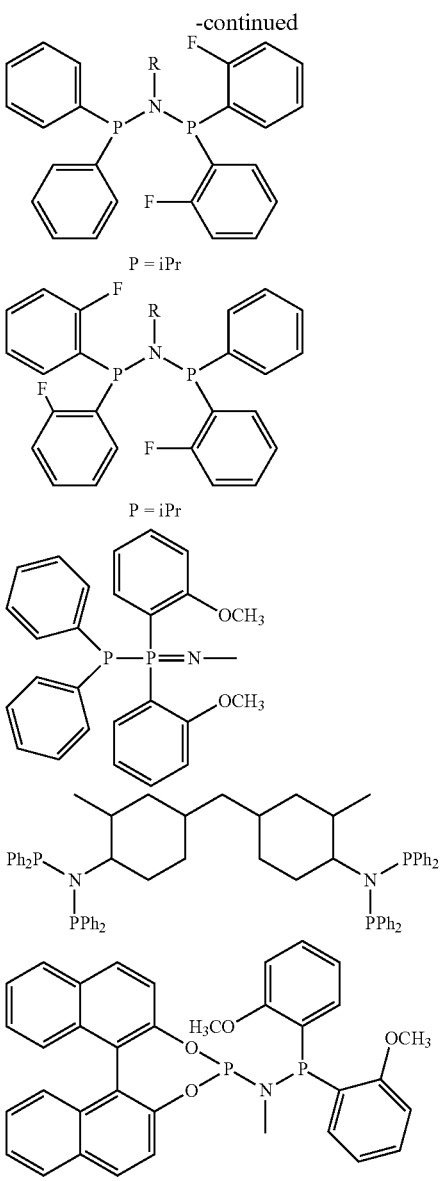

Suitable ligand systems may also include mixtures of the above-mentioned ligands.

The ligating compound may include a polymeric moiety to render the reaction product of the source of transition metal and said ligating compound soluble at higher temperatures and insoluble at lower temperatures e.g. 25° C. This approach may enable the recovery of the complex from the reaction mixture for reuse and has been used for other catalyst as described by D.E. Bergbreiter et al., *J. Am. Chem. Soc.*, 1987, 109, 177-179. In a similar vein these transition metal catalysts can also be immobilised by binding the ligating compound to silica, silica gel, polysiloxane or alumina backbone.

The ligating compound may include multiple ligating units or derivatives thereof. Non-limiting examples of such ligands include dendrimeric ligands as well as ligands where the individual ligating units are coupled either via one or more of the R groups or via the linking group Y. More specific, but not limiting, examples of such ligands may include 1,2-di-(N(P(phenyl)$_2$)$_2$)-benzene, 1,4-di-(N(P(phenyl)$_2$)$_2$)-benzene, N(CH$_2$CH$_2$N(P(phenyl)$_2$)$_2$)$_3$, 1,4-di-(P(phenyl)N(methyl)P(phenyl)$_2$)-benzene, 1,2-di-(N(P(p-methoxyphenyl)$_2$)$_2$)-benzene, 1,4-di-(N(P(p-methoxyphenyl)$_2$)$_2$)-benzene, N(CH$_2$CH$_2$N(P(p-methoxyphenyl)$_2$)$_2$)$_3$ and 1,4-di-(P(p-methoxyphenyl)N(methyl)P(p-methoxyphenyl)$_2$)-benzene.

The ligating compounds may be prepared using procedures known to one skilled in the art and procedures forming part of the state of the art.

Figure 2:
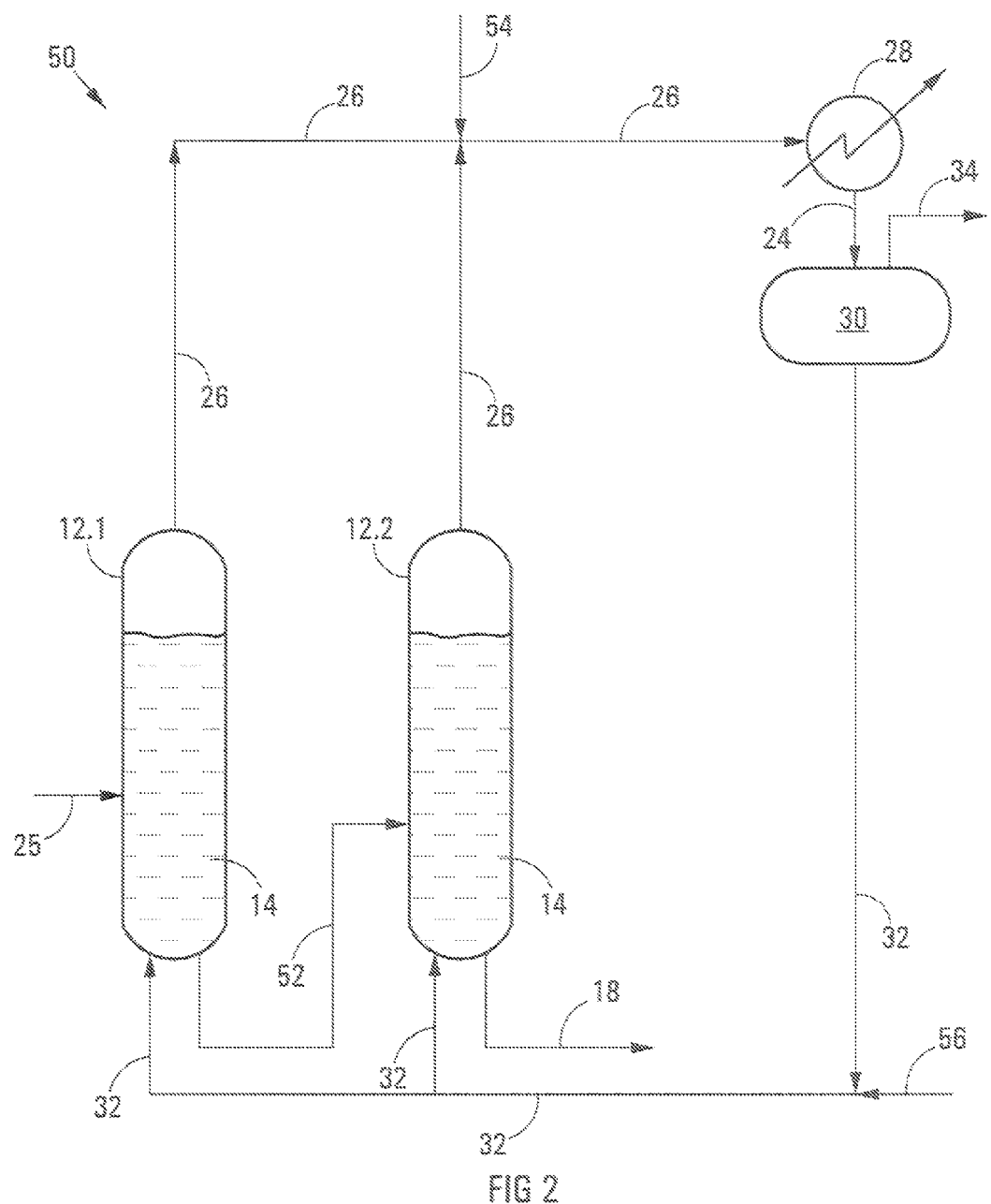
Figure 3:
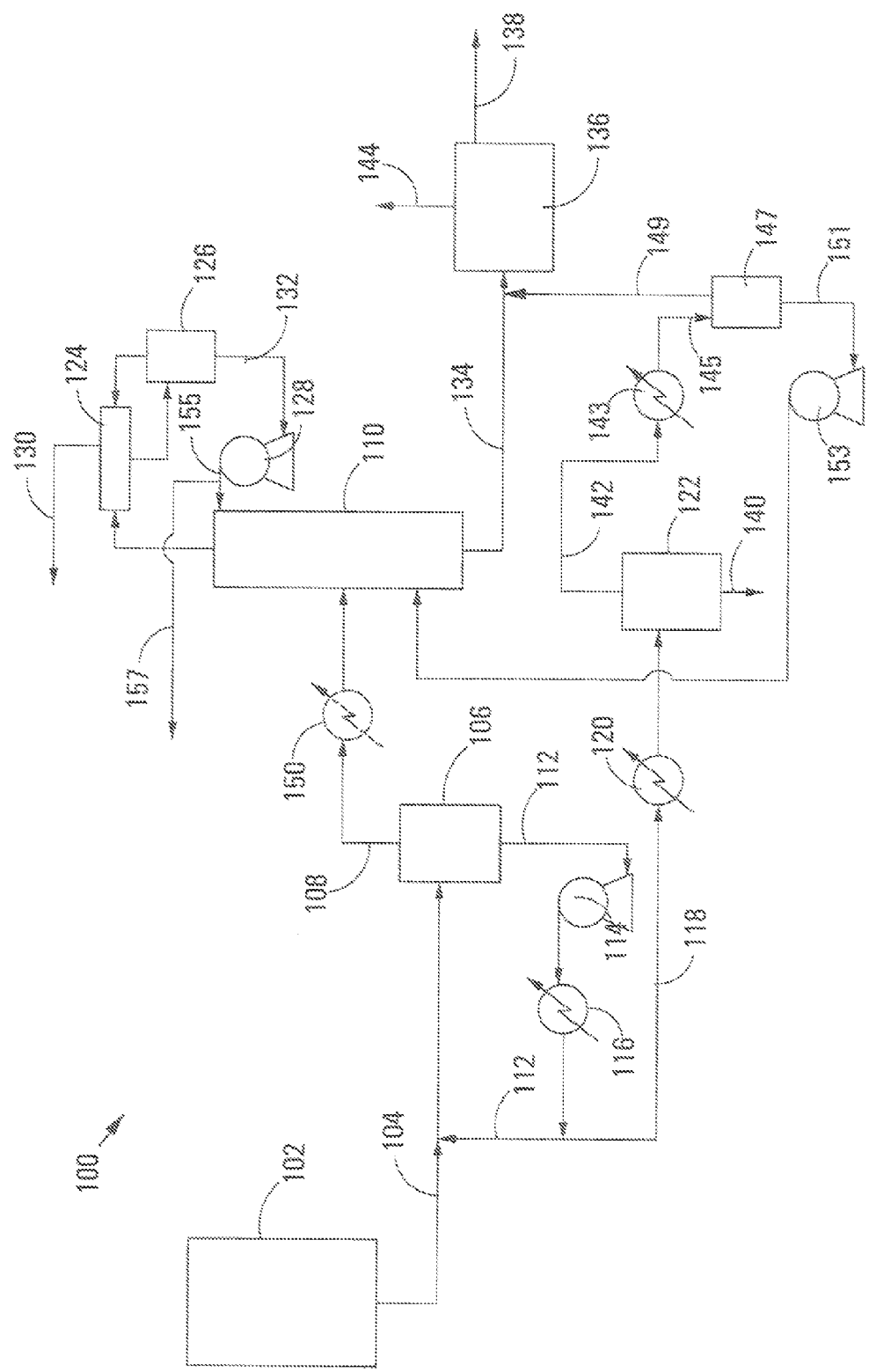
Figure 4:
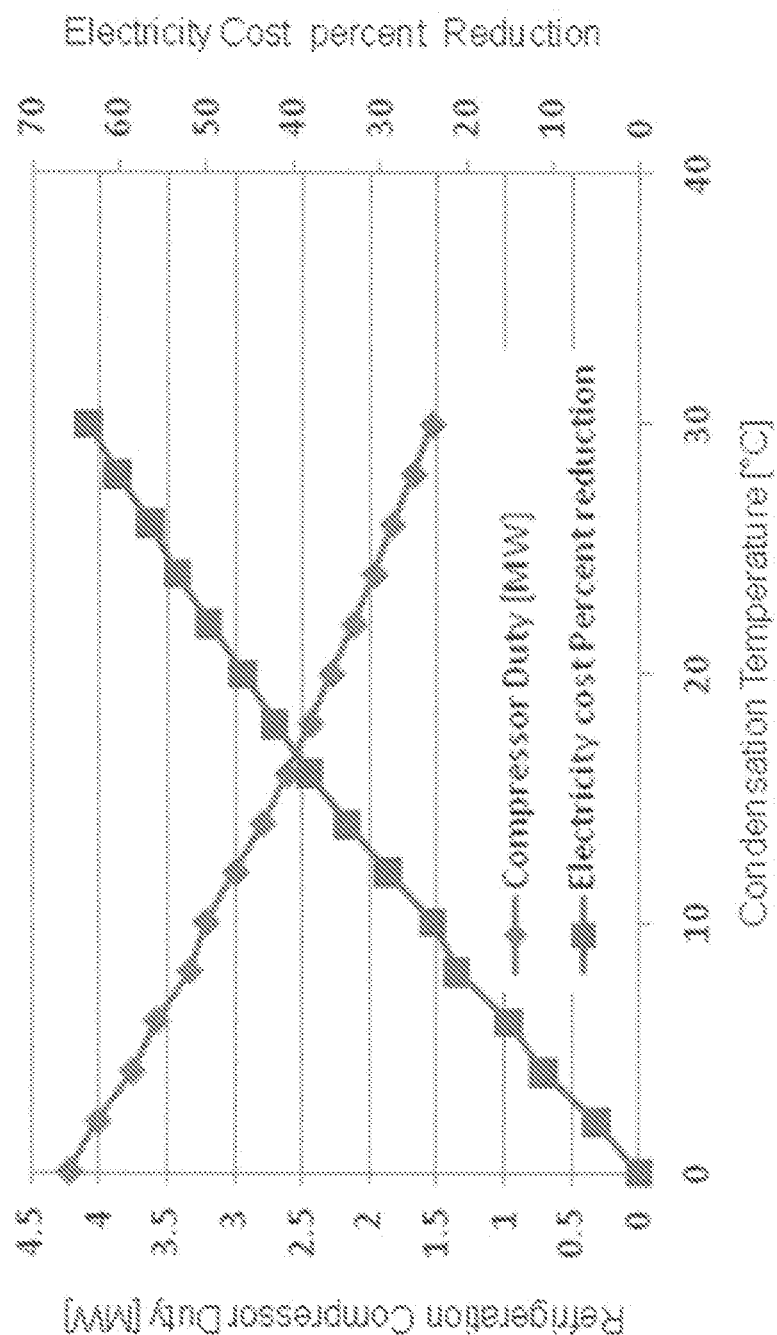
Figure 5:
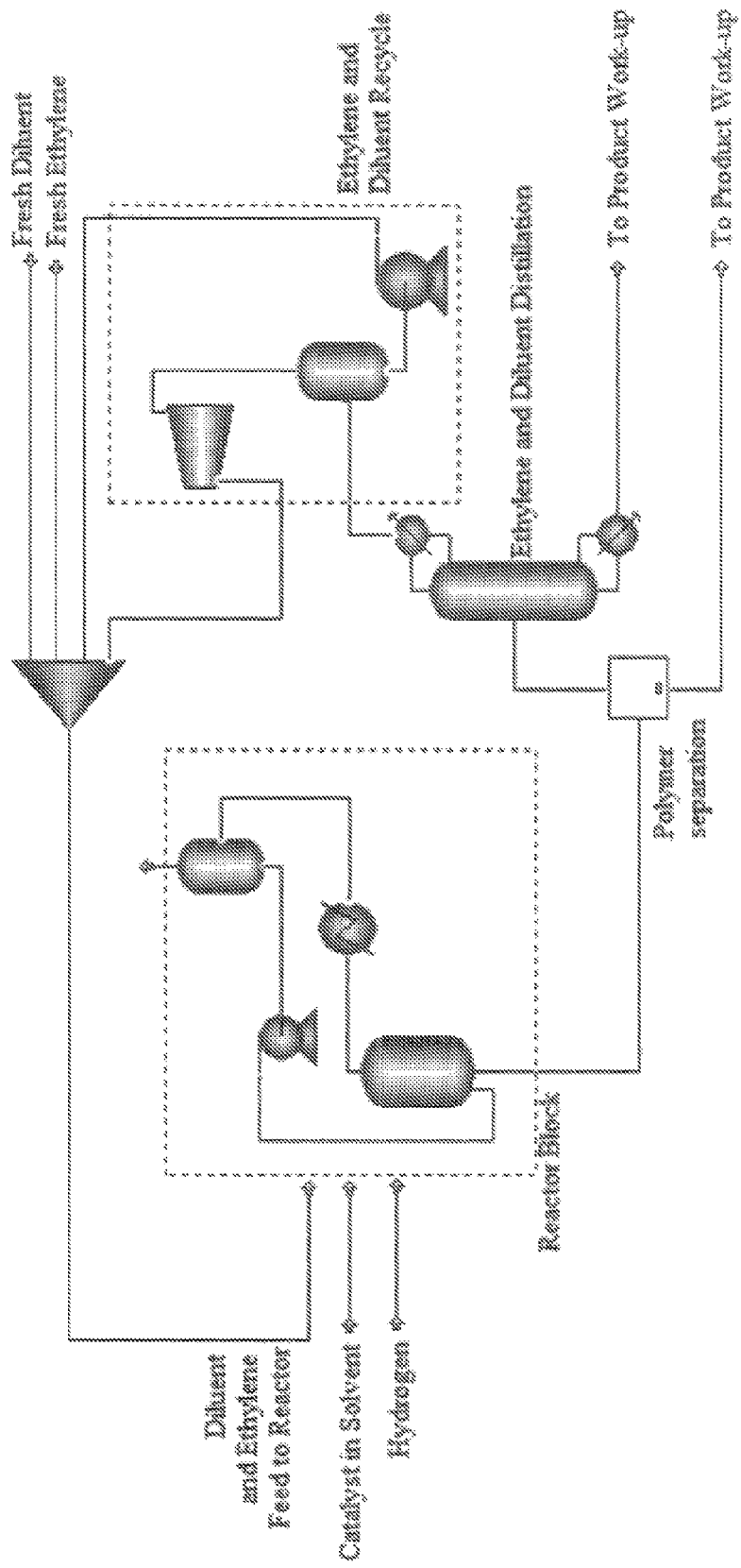
Figure 6:
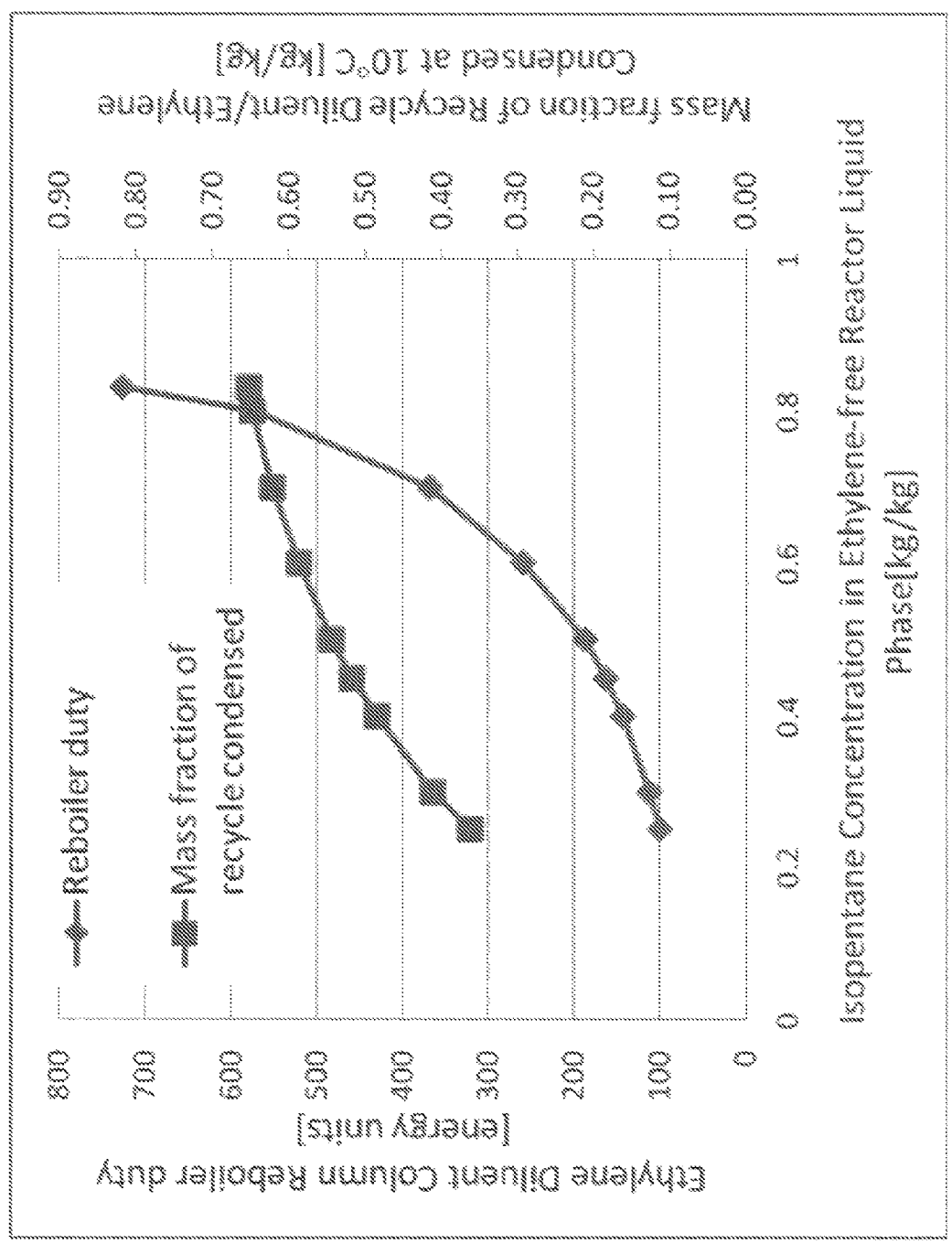
Figure 7:
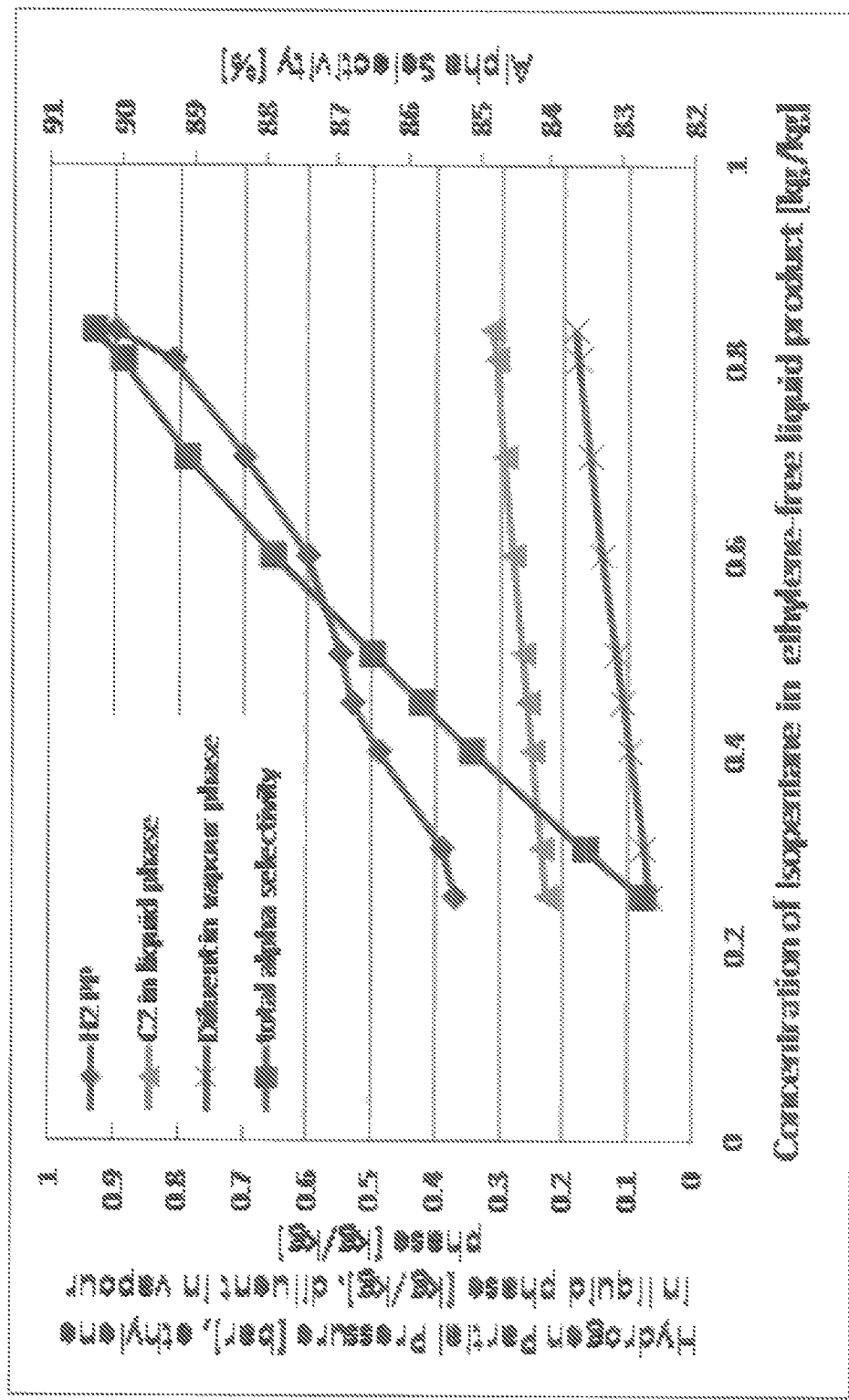

The invention will now be described, by way of example, with reference to simulations provided in Examples 1 and 2 and with reference to the accompanying drawings in which FIG. 1 shows one embodiment of a process in accordance with the invention for oligomerising a hydrocarbon to form at least one co-monomer product;

FIG. 2 shows another, more complex embodiment of a process in accordance with the invention for oligomerising a hydrocarbon to form at least one co-monomer product;

FIG. 3 shows yet another embodiment of a process in accordance with the invention for oligomerising a hydrocarbon to form at least one co-monomer product; and FIG. 4 shows graphs of refrigeration compression duty and electricity cost reduction as a function of condensation temperature of gaseous components withdrawn from a head space above a bulk liquid phase of a bubble column reactor employed as the oligomerisation reactor in a process in accordance with the invention for oligomerising a hydrocarbon to form at least one co-monomer product;

FIG. 5 shows a flow sheet of a process simulated in Example 2;

FIG. 6 shows graphs of an ethylene/diluent solvent recovery distillation column reboiler duty and fraction of recycle condensed as a function of organic liquid diluent solvent concentration in a reactor liquid phase for the process simulated in Example 2; and FIG. 7 shows graphs of the impact of organic liquid diluent solvent concentration in reactor liquid phase on total alpha selectivity, hydrogen partial pressure at which all reactor vapour can be condensed at specified conditions, ethylene concentration in a liquid phase and diluent solvent concentration in a vapour phase for the process simulated in Example 2.

Referring to FIG. 1 of the drawings, reference numeral 10 generally indicates a process in accordance with the invention for oligomerising a hydrocarbon to form at least one co-monomer product. The process 10 as shown in the drawing is in particular for the tetramerisation, and to a lesser extent trimerisation, of ethylene but it can also be used for the oligomerisation of other olefinic feedstocks.

The process 10 includes a reactor 12 containing a bulk liquid phase 14 in the form of a bubbling column. The reactor 12 is thus a bubble column reactor. Recycled condensed liquid ethylene as hydrocarbon reactant and recycled organic liquid diluent solvent (in liquid form) including at least one diluent solvent such that at least 70% by mass of the diluent solvent has a normal boiling point below the normal boiling point of 1-hexene (63° C.) but above −20° C., e.g. isobutane (normal boiling point −11.7° C.), 2-2, di-methylpropane (neopentane) (normal boiling point 9.5° C.) or 2-methylbutane (isopentane) (normal boiling point 27° C.) enter the bottom of the reactor 12 from a line 32 so that the condensed liquid ethylene and organic liquid diluent solvent in use enter the bottom of the bubbling column of bulk liquid phase 14. A catalyst line 25 leads into the reactor 12 to feed a catalyst mixture or catalyst system which includes a chrome catalyst dissolved in at least one catalyst solvent which differs from the organic liquid diluent solvent, into the reactor 12. In the process 10 of the invention, the at least one catalyst solvent and the organic liquid diluent solvent are not the same as they are selected to fulfil different purposes. The catalyst solvent is selected to facilitate dissolution of the catalyst to form a catalyst solution, i.e. a dissolved catalyst mixture that can easily be transported to the reactor 12 and dispersed inside the reactor 12, while the organic liquid diluent solvent is selected to facilitate or promote ethylene solubility in the liquid phase and increase the condensation point temperature of an ethylene-rich overheads gaseous product stream (see below) withdrawn from the reactor 12. Typically, chrome catalysts are poorly soluble in the organic liquid diluent solvents listed above. Both catalyst and organic liquid diluent solvents are selected to facilitate the separation of a liquid reactor product slate into on-specification oligomerisation products. In the case of the catalyst solvent this may be achieved by using one of the oligomerisation products as catalyst solvent. This is not the case for the organic liquid diluent solvent, which must be inert.

The ratio of organic liquid diluent solvent to catalyst solvent must be optimised to fulfil the following criteria; there must be sufficient catalyst solvent to ensure that the chrome catalyst is completely dissolved, but not too much so that the catalyst solvent dilutes the organic liquid diluent solvent to the extent that the benefit of higher ethylene solubility in the selected organic liquid diluent solvent is negatively impacted.

A liquid phase withdrawal line 18, preferably with a bottom withdrawal point on the reactor 12, leads to a treatment stage 20, with an oligomeric product line 22 (in use containing at least one co-monomer product and oligomeric by-product), a gaseous ethylene and gaseous or vapourised organic diluent solvent recycle line 24, a liquid ethylene and organic liquid diluent solvent recycle line 57 and a solids line 27 leaving the treatment stage 20. A gaseous components line 26 leaves from a top of the reactor 12 to a partial condenser 28 (which in an alternative embodiment of the process of the invention may be a complete condenser) and leads from the partial condenser 28 to a separator 30. The gaseous recycle line 24 and the liquid recycle line 57 from the treatment stage 20 join the gaseous components line 26 leading into the partial condenser 28. An organic liquid diluent solvent make-up line 56 joins the line 32 and a fresh gaseous ethylene line 54 joins the recovered ethylene and diluent solvent line 24.

The organic liquid diluent solvent may be supplied to the process 10 as a liquid or may first need to be condensed (not shown). The organic liquid diluent solvent make-up line 56 may thus alternatively be introduced before the partial condenser 28 (not shown), particularly if the organic liquid diluent solvent is in gaseous form and has to be condensed before being fed to the reactor 12.

The line 32 is thus a condensed liquid ethylene and an organic liquid diluent solvent (in liquid form) recycle line which leads from the separator 30 to the reactor 12, with a gaseous purge line 34 also leading from the separator 30. Typically, the condensed liquid ethylene and organic liquid diluent solvent in the line 32 are at a temperature of less than about 35° C.

In order to trimerise and tetramerise ethylene to produce 1-hexene and 1-octene, condensed liquid ethylene (predominantly recycled but with a small portion of fresh ethylene) and organic liquid diluent solvent are fed by means of the line 32 into the bottom of the bulk liquid phase 14 inside the reactor 12. The reactor 12 is operated typically at a pressure of between about 45 bar(a) and 50 bar(a), with the bulk liquid phase 14 being at a temperature below its boiling point at the operating pressure of the reactor 12. Typically, this temperature is about 60° C.

The bulk liquid phase 14 of the bubble column reactor 12 includes an admixture of ethylene, oligomeric products and by-products (including at least one co-monomer product), at least one catalyst solvent which includes a dissolved catalyst system, organic liquid diluent solvent, and small amounts of polymeric solids formed by undesirable side reactions.

Typical mass concentrations dissolved in the liquid phase 14 are about 20 to about 35 mass % ethylene, about 25 to about 60 mass % oligomeric product and by-product and about 40 to about 80 mass % organic liquid diluent solvent. The bulk liquid phase 14 will contain at least one catalyst solvent as well wherein the mass ratio of organic liquid diluent solvent to catalyst solvent introduced to the bubble column reactor 12 via the recycle diluent solvent recovered from the reactor liquid product (from line 24), the catalyst solution feed stream (in line 25) and the fresh diluent solvent make-up stream (in line 56) is between about 15:1 and about 4500:1, more preferably between about 150:1 and about 1500:1 and most preferably between about 500:1 and about 1500:1. The mass fraction of organic liquid diluent solvent in ethylene in the feed line 32 is typically between about 0.1 and about 0.5, more preferably between about 0.2 and about 0.3.

Fast rising bubbles of vapourised ethylene and organic liquid diluent solvent pass upwardly through the column of the bulk liquid phase 14, ensuring that the column bubbles and that the column exhibits high turbulence.

In the embodiment of the invention shown in FIG. 1, the catalyst system comprises Cr (chromium), (phenyl)$_2$PN(isopropyl)P(phenyl)$_2$ ligand and methyl aluminoxane as activator.

The reactor 12 with the particular catalyst system primarily produces 1-hexene and 1-octene from ethylene. Preferably the process 10 produces at least 30% octene. In other words, the reactor 12 primarily tetramerises and to a lesser extent trimerises the ethylene. The oligomerisation reactions taking place inside the reactor 12 are exothermic. The specific heat required to heat the incoming liquid ethylene and organic liquid diluent solvent in the line 32 to 60° C. together with the latent heat of vapourisation required to evaporate the liquid ethylene and organic liquid diluent solvent is sufficient to remove the heat of reaction to maintain the bulk liquid phase 14 at a temperature below its boiling temperature but above the boiling temperature of the liquid ethylene and organic liquid diluent solvent mixture thereby to vapourise liquid ethylene and organic liquid diluent solvent in the bulk liquid phase 14 ensuring that the bulk liquid phase 14 is in the form of a bubbling column. The vapourisation of the liquid ethylene and organic liquid diluent solvent and hence the formation of fast rising gas bubbles creates vigorous mixing inside the bulk liquid phase 14, turning the bulk liquid phase 14 into a bubbling column. This is important and advantageous in the embodiment of the invention shown in FIG. 1, as it may allow the reactor 12 to operate without a stirrer or agitator, which, if present, may be susceptible to fouling. Temperature control of the reactor 12 is effected by means of flashing of liquid ethylene and organic liquid diluent solvent in the bulk liquid phase 14 so that in at least this embodiment there is no need for a heat exchanger in direct contact with the bulk liquid phase 14 to remove heat from the bulk liquid phase 14 (i.e. direct-contact cooling or so-called "hot cooling" is employed, using the organic liquid diluent solvent as an evaporative cooling medium in combination with evaporation of excess liquid ethylene reactant).

The liquid phase in the reactor 12 is withdrawn through the liquid phase withdrawal line 18 to maintain the bulk liquid phase 14 at a desired level within the reactor 12. A catalyst kill reagent, e.g. an alcohol such as ethanol, or water, may be introduced (not shown) to the withdrawn liquid product stream to prevent further reaction. The liquid phase is treated in the treatment stage 20, providing an unreacted or recovered gaseous ethylene and vapourised organic liquid diluent solvent stream which is withdrawn along line 24 and an unreacted or recovered liquid ethylene and organic diluent solvent stream which is withdrawn along line 57, both of which are eventually returned in liquid form to the reactor 12 (together with any make-up liquid diluent solvent fed by means of the make-up diluent solvent line 56 and fresh ethylene fed by means of the gaseous ethylene line 54), via the condenser 28, the separator 30 and the recycle line 32.

An oligomeric product stream consisting of a mixture of desirable oligomeric products and less valuable oligomeric by-products is withdrawn from the treatment stage 20 by means of the oligomeric product line 22, and small amounts of solids are separated and withdrawn through the solids line 27.

In FIG. 1, the treatment stage 20 is represented by a single block. In practice, the separation of unreacted ethylene and organic liquid diluent solvent, oligomeric products, oligomeric by-products and polymeric solids that may have formed from the liquid phase requires a complex series of separation steps typically including at least one distillation operation and at least one, typically two flash stages, typically one condensation stage, typically one or more adsorption purification stages and possibly one or more pressure-increasing stages (e.g. pumps or compressors). More detail on this aspect of the process of the invention is provided with reference to FIG. 3.

Gaseous components, including unreacted vapourised ethylene and vapourised organic diluent solvent and any gaseous product that may have formed in the reactor 12, are collected in a head space above the bulk liquid phase 14 and withdrawn through the gaseous components line 26. The gaseous components may also include light additives such as hydrogen, trace amounts of oligomerisation product and by-product, light impurities such as methane which may have entered the process 10 with the ethylene feed and ethane formed in the reactor 12 as a by-product. Methane may also be liberated in a catalyst deactivation reaction, particularly when the catalyst includes an aluminium specie, as a result of the reaction of an alcohol with the aluminium specie. The partial pressure of light impurities, e.g. methane and ethane, in the reactor 12 should be minimised as far as practically possible, to increase the ethylene partial pressure thereby increasing the ethylene concentration in the bulk liquid phase 14, and hence increasing the productivity of the reactor 12.

As will be appreciated, as ethylene has a very low boiling point (normal boiling point −103.7° C.), even at reactor pressures of >45 bar, for organic liquid diluent solvents heavier-boiling than 1-hexene but with a normal boiling point of −20° C. or less, the overheads stream in the gaseous components line 26 must be cooled to the range of −5 to 2° C., with the specific value dependent on the concentration of light components such as ethane, methane and hydrogen in the reactor overheads, in order to condense most of the reactor overheads, unless something is done to increase the condensation temperature of the reactor overheads. In the process of the invention, an organic liquid diluent solvent with a normal boiling point below the normal boiling point of 1-hexene but above −20° C. is used to increase the condensation temperature of the reactor overheads.

Thus, in the partial condenser 28 (which may be a total condenser), the gaseous components withdrawn along the gaseous components line 26 are cooled, forming a mixture of condensed ethylene and diluent solvent which is knocked out in the separator 30 and returned as a liquid fraction to the reactor 12 by means of the liquid ethylene recycle line 32. As indicated hereinbefore, instead of partially condensing the gaseous components, the gaseous components may in an alternative embodiment of the invention be condensed fully. Selection of an appropriate organic liquid diluent solvent which is volatile enough to report to the ethylene-rich reactor vapour overheads, but sufficiently heavy boiling in comparison to ethylene to increase the required condensation temperature is important. Thus, advantageously, by selecting appropriate operating conditions and an appropriate organic liquid diluent solvent concentration in the bulk liquid phase 14, it is possible to raise the condensation point temperature of the ethylene and organic liquid diluent solvent mixture sufficiently high. Advantageously, with a condensation point temperature in the order of, say 10° C. to 30° C., even with hydrogen being present, it is possible to cool the gaseous components withdrawn from the head space above the bulk liquid phase 14 with a single stage absorption refrigeration system, instead of a compressor-based refrigeration system or two-stage absorption refrigeration system. As such, refrigeration capital and operating costs can be reduced significantly.

Simulation results show that the organic liquid diluent solvents used in the process of this invention can comprise 20-35% of the vapour overheads streams for reactor pressures in the range 40-50 bar(a) and reactor temperatures of 50-70° C. The presence of these components makes manipulation of reactor pressure to obtain a desired condensation temperature of the vapour overheads feasible. To illustrate this point, Table 1 shows the effect of concentration and pressure of organic liquid diluent solvents potentially useful in the process of the invention on the condensation temperature of an ethylene/ethane/organic liquid diluent solvent stream with and without 0.5 bar of hydrogen added, and also include comparative information for propane, which falls outside the scope of the invention, as organic liquid diluent solvent.

TABLE 1

Condensation temperature required at various organic liquid diluent solvent concentrations and reactor pressure

| Concentration of diluent solvent in reactor overheads [mass %] | Reactor pressure [bar] | No diluent solvent | Propane | Isobutane | Isopentane | Neopentane |
|---|---|---|---|---|---|---|
| | | Required condensation temperature for case of no hydrogen for various diluent solvents [° C.] | | | | |
| 15 | 40 | −1.2 | 5.7 | 5.4 | 4.5 | 4.6 |
| | 45 | 3.9 | 11.7 | 11.5 | 10.6 | 10.7 |
| | 50 | 8.8 | 19.8 | 17.6 | 16.5 | 16.7 |
| | 55 | — | 25.1 | 21.7 | 22.7 | 21.2 |

TABLE 1-continued

Condensation temperature required at various organic liquid diluent solvent concentrations and reactor pressure

| Concentration of diluent solvent in reactor overheads [mass %] | Reactor pressure [bar] | No diluent solvent | Propane | Isobutane | Isopentane | Neopentane |
|---|---|---|---|---|---|---|
| 20 | 40 | −1.2 | 8.2 | 7.9 | 6.5 | 6.8 |
|  | 45 | 3.9 | 14.4 | 14.2 | 12.8 | 13.1 |
|  | 50 | 8.8 | 20.5 | 20.5 | 18.9 | 19.4 |
|  | 55 | — | 29.0 | 26.3 | 25.0 | 25.7 |
| 25 | 40 | −1.2 | 10.9 | 10.5 | 8.7 | 9.1 |
|  | 45 | 3.9 | 17.4 | 17.1 | 15.2 | 15.7 |
|  | 50 | 8.8 | 23.7 | 23.7 | 21.5 | 22.2 |
|  | 55 | — | 33.1 | 30.4 | 27.8 | 28.8 |
| Required condensation temperature for case of 0.5 bar partial pressure hydrogen for various diluent solvents [° C.] | | | | | | |
| 15 | 40 | −10.9 | −6.8 | −7.3 | −9.8 | −8.4 |
|  | 45 | −2.0 | 3.1 | 3.0 | 0.9 | 1.9 |
|  | 50 | 5.2 | 11.3 | 11.5 | 9.3 | 10.2 |
|  | 55 | 1.7 | 21.3 | 19.3 | 16.8 | 17.9 |
| 20 | 40 | −10.9 | −4.4 | −6.0 | −9.0 | −7.0 |
|  | 45 | −2.0 | 6.1 | 4.8 | 2.1 | 3.6 |
|  | 50 | 5.2 | 14.7 | 13.7 | 10.9 | 12.3 |
|  | 55 | 1.7 | 26.7 | 21.8 | 18.8 | 20.3 |
| 25 | 40 | −10.9 | −2.2 | −4.4 | −8.2 | −5.6 |
|  | 45 | −2.0 | 8.6 | 6.8 | 3.3 | 5.4 |
|  | 50 | 5.2 | 17.5 | 16.1 | 12.6 | 14.5 |
|  | 55 | 1.7 | 24.7 | 24.5 | 20.8 | 22.8 |

Thus, as illustrated by Table 1, for typical reactor operating pressures of 45-55 bar(a), an organic liquid diluent solvent concentration of no more than 25% by mass in the vapour entering the partial condenser 28 will allow condensation temperatures in the range of about 3° C. to about 25° C., even with 0.5 bar hydrogen partial pressure. The lower limit of the organic liquid diluent solvent concentration required still to allow a single-stage absorption refrigeration process for the partial condenser 28 will naturally be affected by the concentration of other inert lights, such as methane and ethane, in the gaseous stream entering the partial condenser 28.

Apart from direct cost savings on the evaporative cooling system employed by the process of the invention when an appropriate organic liquid diluent solvent is used to assist with evaporative cooling of the bulk liquid phase 14 (i.e. the possibility to use a single-stage absorption refrigeration process for the condenser 28 instead of a compressor based refrigeration system), an indirect effect is that of the higher solubility of ethylene in the organic liquid diluent solvents (i.e. diluent solvents with a normal boiling point between −20° C. and 63° C.) compared to that of ethylene in the olefinic tetramerisation product or higher boiling aliphatic diluent solvents (i.e. diluent solvents with a normal boiling point above 63° C.) as is shown in Table 2.

TABLE 2

Simulated ethylene solubilities in various organic liquid diluent solvents and 1-octene at various pressures at 60° C. using the Peng-Robinson Equation of State.

| Pressure (bar(a)) | Propane % | Isobutane % | Isopentane % | Neopentane % | Iso-octane % | 1-Octene % |
|---|---|---|---|---|---|---|
| 40 | 21.1 | 28.0 | 26.8 | 27.4 | 18.5 | 17.3 |
| 45 | 27.3 | 33.0 | 31.3 | 32.3 | 21.7 | 20.2 |
| 50 | 34.0 | 39.0 | 36.2 | 37.6 | 25.1 | 23.2 |

As illustrated by Table 2, for the same oligomeric product to organic liquid diluent solvent ratio, the ratio of ethylene concentration to co-monomer concentration in the reactor bulk liquid phase 14 is higher for the organic liquid diluent solvents used in the process of the invention. Therefore, for a constant production of co-monomer product, the rate of secondary product formation is lower. This results in a lower overall heat of reaction that must be removed for a given co-monomer production rate, which decreases the amount of refrigeration required. Additionally it allows a larger fraction of the feed ethylene to be converted to high value co-monomer oligomerisation products and a lower fraction to the lower value secondary incorporation products.

A person skilled in the art of the invention utilising the prior art available would be led to use propane as a diluent as illustrated in Table 1. The simulation results in Table 2 however show that the concentration of ethylene in the reactor liquid phase when using propane as diluent is surprisingly lower than it is for isobutane and isopentane. Also, in some embodiments, not described here, it may be required to purge a portion of the recycled ethylene/diluent stream to the reactor in order to limit ethane build-up. In such a scenario, it may be desirable first to separate the diluent from the ethylene and ethane via distillation to minimise diluent losses to the process. In said scenario, implementing propane as diluent is not desirable as it is closer boiling to ethane than isobutane and isopentane, resulting in a much more difficult separation.

The combined and synergistic effect of the increased solubility of ethylene in the bulk liquid phase 14 and the increased condensation temperature which can be used in the condenser 28 as a result of appropriate selection and use of the organic liquid diluent solvent on the required energy costs for a compressor-based refrigeration system is portrayed in FIG. 4.

Uncondensed gaseous components, i.e. gaseous product and some gaseous inerts, are withdrawn as a vapour fraction from the separator 30 by means of a gaseous purge line 34.

Although not shown in FIG. 1 of the drawings, the process 10 may include treating the gaseous product withdrawn by means of the gaseous purge line 34 to recover uncondensed unreacted ethylene and possibly uncondensed organic liquid diluent solvent from the gaseous purge. Typically, such a treatment will include at least one distillation stage operating at a lower pressure than the reactor 12, producing ethylene and organic liquid diluent solvent which can either be recycled to the condenser 28 or to the reactor 12. The process may also include using the gaseous components in the purge line 34, which typically includes ethane, as a feed to an ethane cracker or the product work-up section of an ethane cracker facility.

Naturally, the process 10 may include treating the oligomeric product from the treatment stage 20 to separate desired components, such as 1-hexene, 1-octene, a cyclic $C_6$ product and a $C_{10}+$ product and catalyst solvent. Such separation will typically take place in distillation columns, and may of course also form part of the treatment stage 20.

Should the catalyst solvent be one of the desirable oligomeric products, such as 1-hexene, a portion of the appropriate oligomeric product stream will be recycled to a catalyst make-up section (not shown). Should the catalyst solvent not be one of the oligomeric products, it will typically exit with one of the oligomeric by-product streams, having been selected to facilitate separation from the desirable oligomeric product.

Referring to FIG. 2 of the drawings, a more complex embodiment of the process in accordance with the invention is generally indicated by reference numeral 50 (but still not providing detail of process operations downstream of any oligomerisation reaction stages). In FIG. 2, the same reference numerals have been used as far as possible as have been used in FIG. 1 to indicate the same or similar parts or features.

The process 50 includes two reactors 12.1 and 12.2. The reactors 12.1 and 12.2 are in series as far as the bulk liquid phase 14 is concerned and a liquid phase transfer line 52 is thus provided to transfer liquid phase from the reactor 12.1 to the reactor 12.2. As far as the condensed liquid ethylene feed is concerned, the reactors 12.1 and 12.2 are however in parallel so that the liquid ethylene feed (together with organic liquid diluent solvent) enters both reactors 12.1 and 12.2 at their bottoms, via line 32.

Liquid phase is transferred from the reactor 12.1 to the reactor 12.2 by means of the liquid phase transfer line 52 (where the impetus for transfer is provided by a difference in pressure between reactors 12.1 and 12.2), before being withdrawn by means of the liquid phase withdrawal line 18. Recycled condensed liquid ethylene and organic liquid diluent solvent and fresh ethylene feed introduced by means of the gaseous ethylene feed line 54 are however fed in parallel by means of the liquid ethylene recycle line 32 into the bottoms of the reactors 12.1 and 12.2.

Although not shown in FIG. 2, the process 50 may naturally include a treatment stage such as the treatment stage 20 to recover ethylene and organic liquid diluent solvent from the liquid phase withdrawn by means of the liquid phase withdrawal line 18, as well as further treatment stages to recover and recycle catalyst solvent (if necessary) and to recover unreacted ethylene and uncondensed organic liquid diluent solvent from the gaseous product withdrawn by means of the gaseous purge line 34, if desired.

In the case of a bubble column using a suitable evaporative cooling medium, i.e. an admixture of ethylene and organic liquid diluent solvent, such as the process 10, 50, as illustrated, the use of lower cost cooling processes for the condensation of the bulk of the gaseous components withdrawn from the bulk liquid phase 14 is possible, which provides a significant capital and operating cost advantage for the process 10, 50, as illustrated, compared to conventional processes for oligomerising a hydrocarbon.

Referring to FIG. 3 of the drawings, yet another embodiment of a process in accordance with the invention for oligomerising a hydrocarbon to form at least one co-monomer product, is shown and generally indicated by reference numeral 100.

FIG. 3 provides more information on the process operations surrounding, and downstream of a reactor in which ethylene is tetramerised and/or trimerised. In FIG. 3, the oligomerisation reactor is indicated by reference numeral 102. It is to be appreciated that the reactor 102 may be the same as or similar to the reactor 12 or the reactors 12.1, 12.2, as hereinbefore described. In FIG. 3 however, substantially no detail regarding the reactor 102 is provided except to show that bulk liquid phase or liquid product from the reactor 102 is withdrawn by means of a flow line 104 which feeds into a medium pressure flash vessel 106.

A vapour overheads stream line 108 leads from the medium pressure flash vessel 106 and feeds into an ethylene recovery distillation column 110. A liquid bottoms stream line 112 from the medium pressure flash vessel 106 passes through a pump 114 and a steam heater 116 before returning to the medium pressure flash vessel 106 as a result of joining the bulk liquid phase withdrawal line 104.

A low pressure flash vessel feed line 118 splits off from the liquid bottoms stream line 112 downstream of the steam heater 116 and passes through a heater 120 to feed into a low pressure flash vessel 122.

The ethylene recovery distillation column 110 is provided with a partial condenser system 124 (which may comprise two condensation steps), a reflux drum 126 and a pump 128. An ethylene vapour recycle line 130 leaves the partial condenser 124 and is returned to the reactor 102. A reflux line 132 leaves the reflux drum 126 and passes through the pump 128. An increased pressure reflux line 155 leads from the pump 128 to the ethylene recovery distillation column. The increased pressure reflux line 155 may branch off into a flow line 157 which returns to the reactor 102. Alternatively, the flow line 157 may branch off the reflux line 132.

A bottoms stream line 134 from the ethylene recovery distillation column 110 feeds into a product work-up section generally indicated by reference numeral 136. One or more olefinic product lines, represented by the line 138 lead from the product work-up section 136. The product work-up section 136 is also provided with a vapour purge line 144.

The low pressure flash vessel 122 is provided with a polymer bottoms line 140, an overhead vapour line 142 and a partial condenser system 143 (which may instead be a total condenser system and which may include more than one condensation step). A partially condensed vapour line 145 leads from the partial condenser system 143 to a separator 147. An overhead vapour line 149 from the separator 147 joins the bottoms stream line 134 from the ethylene recovery distillation column 110. A liquid line 151 from the separator 147 runs via a pump 153 to the ethylene recovery distillation column 110. The liquid line 151 may join the ethylene recovery distillation column 110 itself, or it may join (not shown) the partial condensation system 124. In the process of this invention, this embodiment is important as it allows for the recovery of organic liquid diluent solvent and ethylene at the operating pressure of the ethylene recovery distillation column 110, eventually allowing it to be recycled to the reactor 102.

In the process 100, ethylene is tetramerised in the reactor 102, in the presence of an organic liquid diluent solvent and a catalyst, dissolved in at least one catalyst solvent, as was hereinbefore described with reference to the reactor 12 or the reactors 12.1, 12.2. The reactor 102 thus typically contains a bulk liquid phase or liquid product as hereinbefore described, typically at a temperature of about 60° C. and a pressure of about 45 bar. Bulk liquid phase, in the form of an admixture of ethylene, oligomeric products, the dissolved catalyst system, the organic liquid diluent solvent and small amounts of polymeric solids formed by undesirable side reactions, is withdrawn by means of the bulk liquid phase withdrawal line 104 and passes to the medium pressure flash vessel 106. Before entering the medium pressure flash vessel 106, the withdrawn bulk liquid phase is heated to a temperature of about 167° C., as a result of being contacted with the heated liquid bottoms stream in the liquid bottoms stream line 112 from the medium pressure flash vessel 106.

In the medium pressure flash vessel 106, the heated bulk liquid phase in the bulk liquid phase withdrawal line 104 is flashed at a pressure less than 30 bar(a), e.g. about 25 bar(a), producing a vapour overheads stream comprising mostly ethylene and organic liquid diluent solvent and co-monomer product, which is withdrawn by means of the vapour overheads stream line 108, and the liquid bottoms stream withdrawn by means of the liquid bottoms stream line 112. The liquid bottoms stream comprises mostly polymer solids and some co-monomer product and organic liquid diluent solvent (and some ethylene) and is pumped up to a pressure higher than the operating pressure of the reactor 102 before it is passed through the steam heater 116 so that the temperature of the liquid bottoms stream in the liquid bottoms stream line 112 is raised to above 190° C., e.g. about 200° C.

As hereinbefore described, a portion of the liquid bottoms stream in the liquid bottoms stream line 112 coming from the steam heater 116 is returned to the bulk liquid phase withdrawal line 104 to heat the withdrawn bulk liquid phase. Another portion is fed by means of the low pressure flash vessel feed line 118 through the heater 120 where it is heated to a temperature of about 265° C. before being fed into the low pressure flash vessel 122. The low pressure flash vessel 122 is operated at a pressure of less than about 10 bar(a), e.g. about 4.5 bar(a) and yields an overhead vapour stream (comprising mostly co-monomer product, with some ethylene and vapourised organic liquid diluent solvent) withdrawn by means of the overhead vapour line 142 and a concentrated polymer stream withdrawn by means of the polymer bottoms line 140. The concentrated polymer stream in the polymer bottoms line 140 includes most of the solids polymeric by-product formed in the reactor 102.

The vapour overhead stream in the vapour overhead stream line 108 from the medium pressure flash vessel 106 is passed through an optional heat integration heat exchanger generally indicated by reference numeral 150, where heat may be removed from the vapour overhead stream in the vapour overhead stream line 108, before the vapour overhead stream enters the ethylene recovery distillation column 110. In the ethylene recovery distillation column 110, ethylene and organic liquid diluent solvent are recovered at pressure in conventional fashion. A vapour overhead stream from the ethylene recovery distillation column 110 is partially condensed in conventional fashion in the partial condenser system 124 and refluxed back to the ethylene recovery distillation column 110 by means of the reflux drum 126, the reflux line 132 and the pump 128. An ethylene and organic diluent solvent vapour stream is withdrawn from the partial condenser system 124 and recycled back to the reactor 102 by means of the ethylene vapour recycle line 130. Typically, this vapour ethylene and diluent solvent stream is compressed to increase pressure to that of the oligomerisation reactor 102, purified in one or more guard beds and then condensed together with a gaseous overheads stream from the reactor 102 in a partial or complete condenser such as the partial condenser 28 shown in FIG. 2, before the recycled ethylene and diluent solvent are returned to the reactor 102 as a liquid mixture. A portion of the reflux of the ethylene distillation column 110, which include ethylene and organic diluent solvent may be split off by means of the flow line 157 and returned to the reactor 102. Typically the pressure of the liquid stream in the flow line 157, which includes ethylene and organic diluent solvent, is conveniently increased to the reactor pressure by means of the pump 128. Alternatively, an additional pump (not shown) in the flow line 157 is used to increase the pressure. As can be appreciated, pumping a portion of the ethylene and organic liquid diluent solvent recycle to the reactor 102 instead of having to compress it in order to recycle it leads to substantial operating and capital savings. Typically the ethylene and organic liquid diluent solvent in the flow line 157 is also purified in one or more guardbeds (e.g. to remove a catalyst kill agent) before being returned to the reactor 102.

A bottoms stream from the ethylene recovery distillation column 110, comprising most of the co-monomer product produced in the reactor 102, is withdrawn by means of the bottoms stream line 134 and fed to the product work-up section 136. The product work-up section 136 is operated at a lower pressure than the ethylene recovery distillation column 110 and typically produces a plurality of olefinic product streams (represented by the flow line 138), such as 1-hexene and 1-octene, by means of distillation. Typically, the product work-up section 136 produces a vapour purge which is purged via the vapour purge line 144.

In the embodiment of the process of the invention shown in FIG. 3 of the drawings, an overhead vapour stream in the overhead vapour line 149 from the separator 147 is combined with the bottoms stream in line 134 from the ethylene recovery distillation column 110 before being fed to the product work-up section 136

The advantages of replacing a heavier-boiling aliphatic solvent with an organic liquid diluent solvent such as isobutane, neopentane or isopentane are clear. Due to the higher volatilities of these products, the flash drums 106 and 122 may be operated at higher pressure or at lower temperature to achieve the required ethylene and organic liquid diluent solvent recovery (in line 130) or polymer solution concentrations (in line 140). The combined energy input via the pump 114 and the steam heater 116 may therefore be significantly reduced as is shown in Table 3.

TABLE 3

Flowsheet impacts of selected diluent solvents on polymer separation and ethylene recycle sections for constant co-monomer production.

|  | Iso-octane | Propane | Isobutane | Isopentane |
|---|---|---|---|---|
| Diluent in reactor product [mass %] | 50 | 50 | 50 | 50 |
| Pressure flash drum 106 [bar(a)] | 15 | 30 | 29 | 20 |
| Temperature flash drum 106 [° C.] | 190 | 160 | 160 | 160 |

TABLE 3-continued

Flowsheet impacts of selected diluent solvents on polymer separation and ethylene recycle sections for constant co-monomer production.

|  | Iso-octane | Propane | Isobutane | Isopentane |
|---|---|---|---|---|
| Duty pump 114 [kW] | 1200 | 248 | 256 | 344 |
| Duty steam heater 116 [MW] | 4.64 | 5.0 | 5.1 | 5.1 |
| Duty heater 120 [MW] | 420 | 262 | 275 | 322 |
| Temperature flash drum 122 [° C.] |  | 186 | 188 | 190 |
| Ethylene column 110 overheads pressure [bar] | 12.5 | 12.5 | 12.5 | 12.5 |
| Ethylene column 110 reboiler duty [MW] | 1.7 | 1.6 | 1.9 | 2.4 |
| Ethylene column 110 cooling water condenser [MW] | 2.0 | 0.1 | 1.2 | 3.8 |
| Ethylene column 110 chiller condenser [MW] | 0.3 | 2.3 | 1.7 | 0 |
| Recycle chiller T | 0 | 12 | 12 | 12 |
| Recycle chiller duty | — | 0 | 1.0 | 0.7 |
| Ethylene recycle compressor [kW] | 1350 | 840 | 650 | 550 |

In the case of a diluent solvent that is heavier boiling than 1-hexene, the overheads of the ethylene recovery column 110 would consist primarily of ethylene, with traces of light inerts such as ethane and methane. In the case of the organic liquid diluent solvents used in the process of the invention, it is possible to recover the organic liquid diluent solvent with the ethylene in the ethylene recovery column 110 for recycle. As such, the overheads of the ethylene recovery column 110 contains a significant concentration of organic liquid diluent solvent and therefore has a higher condensation temperature than is the case if the diluent solvent reports to the bottom stream 134 of the column 110.

It is desirable to limit the reboiler (not shown) temperature of the ethylene recovery column 110 to <230° C. in order to allow the use of high pressure steam as a utility. This necessarily imposes an upper limit in the operating pressure of the column 110. Simulation results show that, for organic liquid diluent solvents such as isobutane, isopentane and neopentane, an appreciable amount of the combined organic liquid diluent solvent/ethylene recycle can be condensed at a process temperature of 12° C., at an ethylene column 110 operating pressure as low as 12.5 bar(a). This implies that an appreciable amount of the combined recycle ethylene/organic liquid diluent solvent stream may be condensed using an absorption/desorption type refrigeration system. As will be appreciated, the advantage to condensing this recycle is that it can be raised to reactor pressure by means of a pump instead of a more expensive compressor.

The impact of a combined organic liquid diluent solvent/ethylene stream on recompression duties is shown in Table 3. Surprisingly, simulations show that, even though the overall flow rate of the vapour recycle stream from the column 110 to the reactor 102 may increase in the case of a combined ethylene/organic liquid diluent solvent stream, the recompression duty required can decrease as the energy required to compress a unit of isobutane, isopentane or neopentane is lower than that required to compress the same unit of ethylene.

It should further be noted that, in the case of propane as organic liquid diluent solvent, temperatures lower than 11° C. would be required to achieve significant condensation of the combined low-boiling organic liquid diluent solvent/ethylene recycle stream for pressures below 12.5 bar(a), i.e. propane does not offer as much of an advantage with respect to recompression savings as do organic liquid diluent solvents with a normal boiling point above −20° C., such as isobutane, neopentane and isopentane.

In the case of an organic liquid diluent solvent boiling between 1-hexene and 1-octene, a topping/tailing distillation sequence is required to isolate the organic liquid diluent solvent for recycle. This separation may be achieved in two columns or in a combined partition (divided-wall) distillation column. The key-component separations in this case would be intermediate-boiling organic liquid diluent solvent/1-octene and $C_6$ cyclics and 1-hexene/intermediate-boiling organic liquid diluent solvent.

If the organic liquid diluent solvent is recovered in the ethylene recovery column, as in the case of the column 110 of the process 100, one column may be removed from the product work-up section 136. In addition, the above key-component separations are replaced by the key-component separation $C_6$ cyclics and 1-hexene/1-octene.

This separation is simpler than both of the separations required in the case of the intermediate boiling organic liquid diluent solvent, i.e. not only is a distillation column removed from the product work-up section 136, it is the larger of the two columns that is removed and a higher 1-octene recovery can be achieved in the remaining column for the same number of theoretical stages and comparative energy input.

To illustrate the above point, simulation results obtained for a two-column sequence for the isolation of an intermediate-boiling organic liquid diluent solvent, isooctane, from a tetramerisation product are compared to those obtained for the separation of 1-hexene/$C_6$ cyclics from 1-octene in Table 4.

TABLE 4

Comparison of distillation capacity required in product work-up section for producing C8+ and C6 product fractions with intermediate- and organic liquid diluent solvents as in the process of the invention

|  | Isooctane as diluent solvent | Organic liquid diluent solvents case as in the process of the invention |
|---|---|---|
| Column 1 | C8/diluent solvent splitter | — |
| Theoretical stages | 43 | — |
| Reboiler duty [MW] | 5.6 | — |
| Diameter [m] | 2.4 | — |
| Column 2 | C6/diluent solvent splitter | C6/C8 splitter |
| Theoretical stages | 30 | 30 |
| Reboiler duty [MW] | 1.7 | 1.4 |
| Diameter [m] | 1.4 | 1.5 |
| 1-Octene recovery | <99% | >99% |

Example 1

A diluent screening study was performed by means of simulation. Isobutane, isopentane, neopentane and cyclopentane were screened for ease of separation from 1-hexene. For this screening study, a typical ethylene tetramerisation reaction at 45 bar, 60° C. and organic liquid diluent solvent concentration of 50% in an ethylene-free liquid phase was simulated. In the simulation, the reactor liquid product was then routed to a polymer separation block. A polymer-free product was then routed to a distillation column simulated to operate at a pressure of 11 bar. In this column, the organic liquid diluent solvent and ethylene are recovered overheads for recycle to the tetramerisation reactor. The relatively high operating pressure of the column is specified to recover ethylene at as high a pressure as is practical in order to reduce compression requirements in recycling it to the tetramerisation reactor.

For the screening study, the feed to the ethylene/diluent solvent recovery distillation column was kept constant apart from the actual organic liquid diluent solvent present. The feed temperature, feed flow rate (44 ton per hour), pressure profile and number of theoretical stages of the column (50 stages) were kept constant. The concentrations of the tetramerisation products as well as that of the organic liquid diluent solvent in the feed stream were kept constant. For each organic liquid diluent solvent, the feed point was optimised. The key component separation in the distillation column was between the organic liquid diluent solvent (reporting to the overheads) and 1-hexene (reporting to a bottoms product). Downstream of this distillation column, 1-hexene is the lightest boiling component of the tetramerisation product slate remaining. As such, unless further purification steps are implemented specifically for further diluent solvent/1-hexene separation downstream, any organic liquid diluent solvent reporting to the bottoms product of the ethylene/diluent solvent recovery distillation column will report to a 1-hexene final product. In order to satisfy a required 1-hexene final product specification, a flow rate of <0.4 kg/h of organic liquid diluent solvent is required in the ethylene/diluent solvent recovery distillation column bottoms product.

In the simulation, the reboiler duty and overheads flow rate of the distillation column were varied in an attempt to achieve the best separation possible between organic liquid diluent solvent and 1-hexene. The results are shown in Table 5.

TABLE 5

Results obtained for ethylene/diluent solvent recovery distillation column for various types of organic liquid diluent solvents lower boiling than 1-hexene

| Diluent | Theoretical stages | Reboiler duty [MW] | Diluent solvent in bottoms product [kg] | 1-hexene recycled to reactor [% of feed to column] | Further diluent solvent/1-hexene separation required |
|---|---|---|---|---|---|
| Isobutane | 50 | 1.4 | <0.1 | 1.0 | No |
| Neopentane | 50 | 1.7 | <0.1 | 1.0 | No |
| Isopentane | 50 | 2.3 | 0.25 | 1.6 | No |
| Cyclopentane | 50 | 20 | 1 | 60 | Yes |

As can be seen, effective separation of isobutane, neopentane (2,2-dimethylbutane) and isopentane from 1-hexene may be achieved at reasonable reboiler duties. It is however not possible to achieve the required specification for cyclopentane at the specified distillation pressure or number of theoretical stages, even at reboiler duties as high as 20 MW. If cyclopentane is used as diluent, further separation steps would be required downstream of the distillation column to separate cyclopentane from 1-hexene, which would result in increased capital and operating expenditure.

In light of the above, it is concluded that, of the light-boiling organic liquid diluent solvents investigated, isopentane, neopentane and isobutane are preferred for an ethylene tetramerisation process.

Example 2

A simulation of a tetramerisation reaction was performed using a kinetic model for a PNP-based ligand. The Cr efficiency implemented was 2.8 MMg prod/g Cr. The reaction was simulated at 48.9 bar absolute and 60° C. The simplified flowsheet is shown in FIG. 5.

In this example, the reactor simulated is a boiling bubble column, with heat of reaction removed by evaporating an excess of liquid ethylene. The evaporated ethylene exits a reactor vessel and is condensed in a reactor overheads system before being returned to the reactor vessel. Any uncondensed vapour is purged. One of the objectives of this example is to determine conditions under which the purge can be minimised or eliminated. External to the simulated reactor block, fresh feed ethylene and organic liquid diluent solvent are combined with recycled ethylene and recycled organic liquid diluent solvent before the combined stream is introduced to the reactor block. Cr catalyst in a suitable catalyst solvent is fed into the reactor block in sufficient quantity to produce a desired 1-octene and 1-hexene (alpha) production rate. Liquid from the reactor block is sent to a polymer removal section (detail not shown). A polymer co-product along with some heavier reactor products is routed to further work-up (not shown). The rest of the reactor effluent, including unreacted diluent solvent and ethylene is routed to a distillation column to recover the diluent solvent and ethylene overheads for recycle. The key component separation in this column is between diluent solvent and 1-hexene. There is a specification on the diluent solvent that may report to a bottoms product which is dependent on a final product 1-hexene specification. For all cases investigated, this specification remains constant. 1-Hexene reporting to the overheads of the distillation column is returned to the reactor where a portion reacts to form secondary lower-value reaction product. As such, the amount of 1-hexene reporting to the recycle is limited to a value kept constant for all cases investigated. One of the objectives of this example is to determine the required reboiler duty of the distillation column to achieve the product specifications for a constant number of stages. The ethylene/diluent solvent overheads product is partially condensed and the resulting liquid pumped back up to reactor pressure. The uncondensed portion of the overheads is compressed back up to reactor pressure. Another objective of this example is to determine the fraction of the overheads that can be condensed at 10° C. The column overheads pressure is kept constant at 11 bar. The two ethylene/diluent solvent recycle streams are then combined with fresh ethylene and fresh diluent solvent feeds and returned to the reactor. There is a purge off the recycle ethylene/diluent solvent streams (not shown) which is kept constant.

In the simulation, the organic liquid diluent solvent concentration in the ethylene-free reactor liquid product was varied from 0.25 to 0.83 by mass and a number of process parameters determined as shown in FIGS. 6 and 7. For the simulation, it was assumed that the Cr catalyst concentration in the catalyst solution was 220 ppm by mass. The organic liquid diluent solvent to catalyst solvent ratios corresponding to the solvent concentration range simulated are given in Table 6.

TABLE 6

Simulated organic liquid diluent solvent:catalyst solvent ratios assuming a Cr concentration of 220 ppm in catalyst solvent

| Organic liquid diluent solvent concentration in ethylene-free reactor liquid product [kg/kg] | Organic liquid diluent solvent:catalyst solvent mass ratio [kg/kg] |
|---|---|
| 0.25 | 219 |
| 0.30 | 295 |
| 0.40 | 488 |
| 0.45 | 624 |
| 0.50 | 779 |
| 0.60 | 1278 |
| 0.70 | 2076 |
| 0.80 | 3557 |
| 0.83 | 4622 |

From FIGS. 6 and 7, the following conclusions were inter alia drawn:
1. For constant temperature and pressure, increasing organic liquid diluent solvent concentration increases both the ethylene concentration in the reactor liquid phase as well as the diluent solvent concentration in the vapour overheads. A higher ethylene concentration results in higher alpha selectivity and higher activity (i.e. for constant catalyst efficiency, smaller reactor volumes result) and a higher diluent solvent concentration in the overheads results in a higher partial pressure of hydrogen that can be accommodated while maintaining the same condenser temperature.
2. At organic liquid diluent solvent concentrations below 0.4 mass fraction, the maximum partial pressure of hydrogen that can be accommodated without needing to purge at 10° C. at pressures lower than the supercritical pressure of ethylene is below 0.5 bar. As a partial pressure of 0.5 bar hydrogen is targeted, this implies that an organic liquid diluent solvent concentration above 0.4 mass fraction is preferred for this example.
3. The higher the organic liquid diluent solvent concentration, the higher the alpha selectivity. An organic liquid diluent solvent concentration of 0.4 mass fraction or larger is required to maintain alpha selectivity above 85%.
4. The increase in total alpha selectivity with increase in organic liquid diluent solvent concentration appears to taper at organic liquid diluent solvent concentrations above 0.6 mass fraction.
5. The reboiler duty of the distillation column required to recover the unreacted ethylene and diluent solvent for recycle increases sharply at organic liquid diluent solvent concentrations above 0.5 mass fraction, particularly at organic liquid diluent solvent concentrations above 0.6 mass fraction. This implies an increase in operating costs.

The simulation study performed for Example 2 confirmed that operation of an ethylene tetramerisation reactor at the given temperature and pressure is feasible for organic liquid diluent solvent concentrations in the ethylene-free liquid phase over the range of 0.25 to 0.83 mass fraction. In order to meet a desired hydrogen partial pressure target of 0.5 bar, organic liquid diluent solvent concentrations of >0.4 mass fraction are however required. With regards to selectivity, ability totally to condense the internal reactor recycle, maximise condensation of the external ethylene/diluent solvent recycle and operating cost of downstream equipment an organic liquid diluent solvent concentration of 0.4 to 0.6 mass fraction in the ethylene-free liquid phase was optimum in this example. For this example, assuming a Cr catalyst concentration of 220 ppm in the catalyst solvent, this implies that an organic liquid diluent solvent to catalyst solvent mass ratio of approximately 500 to 1500 is optimum.

For Example 2, further study was conducted into the effect of catalyst concentration.

Experimental data show that a range of Cr catalyst concentrations is possible. Also, depending on the Cr catalyst efficiencies achieved, the amount of Cr required for a targeted alpha product production will vary. An analysis based on available experimental data was therefore performed, assuming that the conclusions reached above for the optimum organic liquid diluent solvent concentration in the reactor hold. The results are shown in Table 7.

TABLE 7

Analysis of organic liquid diluent solvent:catalyst solvent ratios for a range of demonstrated Cr concentrations in catalyst solvent

| | | | | | | | Demonstrated concentrations of Cr salts for various cases | | |
|---|---|---|---|---|---|---|---|---|---|
| Efficiency [MMgPrd/gCr] | Units of alpha product mu/h | Diluent solvent concentration in degassed liquid m/m | Total alpha % | Total product mu/h | Total diluent solvent mu/h | Total Cr required mu/h | Case 1: Piloted concentration of Cr(acac)3 ppm | Case 2: Maximum demonstrated concentration of Cr(acac)3 in cyclohexane ppm | Case 3: Maximum demonstrated concentration of Cr(acac)3 in 1-hexene ppm |
| 2.8 | 100 | 0.25 | 82.7 | 120.9 | 40.3 | 4.31854E−05 | 11 | 170 | 500 |
| 2.8 | 100 | 0.3 | 83.5 | 119.8 | 51.3 | 4.27716E−05 | 11 | 170 | 500 |
| 2.8 | 100 | 0.4 | 85.1 | 117.5 | 78.3 | 4.19674E−05 | 11 | 170 | 500 |
| 2.8 | 100 | 0.45 | 85.8 | 116.6 | 95.4 | 4.1625E−05 | 11 | 170 | 500 |
| 2.8 | 100 | 0.5 | 86.5 | 115.6 | 115.6 | 4.12882E−05 | 11 | 170 | 500 |
| 2.8 | 100 | 0.6 | 87.9 | 113.8 | 170.6 | 4.06306E−05 | 11 | 170 | 500 |
| 2.8 | 100 | 0.7 | 89.1 | 112.2 | 261.9 | 4.00834E−05 | 11 | 170 | 500 |
| 2.8 | 100 | 0.8 | 90 | 111.1 | 444.4 | 3.96825E−05 | 11 | 170 | 500 |
| 2.8 | 100 | 0.83 | 90.4 | 110.6 | 540.1 | 3.9507E−05 | 11 | 170 | 500 |

TABLE 7-continued

Analysis of organic liquid diluent solvent:catalyst solvent ratios for a range of demonstrated Cr concentrations in catalyst solvent

| | Diluent | | | | | | Diluent:catalyst solvent ratios for different cases | | |
|---|---|---|---|---|---|---|---|---|---|
| Efficiency [MMgPrd/ gCr] | Units of alpha product mu/h | solvent concentration in degassed liquid m/m | Total alpha % | Total product mu/h | Total diluent solvent mu/h | Total Cr required mu/h | Case 1: Piloted concentration of Cr(acac)3 | Case 2: Maximum demonstrated concentration of Cr(acac)3 in cyclohexane | Case 3: Maximum demonstrated concentration of Cr(acac)3 in 1-hexene |
| 2.8 | 100 | 0.25 | 82.7 | 120.9 | 40.3 | 4.31854E−05 | 10 | 159 | 467 |
| 2.8 | 100 | 0.3 | 83.5 | 119.8 | 51.3 | 4.27716E−05 | 13 | 204 | 600 |
| 2.8 | 100 | 0.4 | 85.1 | 117.5 | 78.3 | 4.19674E−05 | 21 | 317 | 933 |
| 2.8 | 100 | 0.45 | 85.8 | 116.6 | 95.4 | 4.1625E−05 | 25 | 389 | 1145 |
| 2.8 | 100 | 0.5 | 86.5 | 115.6 | 115.6 | 4.12882E−05 | 31 | 476 | 1400 |
| 2.8 | 100 | 0.6 | 87.9 | 113.8 | 170.6 | 4.06306E−05 | 46 | 714 | 2100 |
| 2.8 | 100 | 0.7 | 89.1 | 112.2 | 261.9 | 4.00834E−05 | 72 | 1111 | 3267 |
| 2.8 | 100 | 0.8 | 90 | 111.1 | 444.4 | 3.96825E−05 | 123 | 1904 | 5600 |
| 2.8 | 100 | 0.83 | 90.4 | 110.6 | 540.1 | 3.9507E−05 | 150 | 2324 | 6835 |

*mu = mass unit

The above analysis shows that organic liquid diluent solvent to catalyst solvent mass ratios as low as 15:1 are feasible. These low ratios are however achieved at very dilute catalyst concentrations in the catalyst solution, implying high catalyst solution volumes for a required flow rate of actual catalyst. From a catalyst preparation/feed section equipment sizing point of view, it is however preferred that the catalyst solution be as concentrated as possible. For the catalyst solvent examples shown in Table 7 and the efficiency assumed, mass ratios of between 390 and 2100 are therefore preferred.

Obviously, technically feasible higher ratios may be obtained for the preferred organic liquid diluent solvent concentration range by increasing catalyst efficiency or by increasing reactor residence time, but this would entail increasing reactor volume, which implies additional capital cost.

In conclusion, based on the above, the use of an organic liquid diluent solvent including at least one organic liquid diluent solvent such that at least 70% by mass of the organic liquid diluent solvent has a normal boiling point below the normal boiling point of 1-hexene but above −20° C., such as isobutane, isopentane and neopentane brings the following advantages in a process 10, 50, 100 as illustrated:
- Higher ethylene solubility in the reactor bulk liquid phase and therefore higher activities and reduced secondary product formation, i.e. formation of undesirable longer chain products of less value. This can decrease reactor size as well as allow the use of a lower organic liquid diluent solvent fraction in the reaction mixture
- Higher mixture condensation temperatures in the evaporative cooling refrigeration system for the reactor vapour overheads as these components are heavier boiling than ethylene while still volatile enough to report to the reactor vapour overheads. This leads to a saving in refrigeration costs
- Less energy input to separate the organic liquid diluent solvent and alpha monomer or co-monomer product due to the higher volatility of these organic liquid diluent solvents
- Reduction in recompression costs as the organic liquid diluent solvents are recycled with the unreacted ethylene, allowing condensation of a portion of the recycle stream. In addition, less energy is required to compress an organic liquid diluent solvent with a normal boiling point below the normal boiling point of 1-hexene but above −20° C., such as isobutane and isopentane than is required to compress ethylene
- Reduction in required distillation steps as the organic liquid diluent solvent is recovered with the ethylene in a single distillation column, eliminating the need for an extra distillation column downstream
- Reduction in required distillation capacity downstream as the separation between an intermediate-boiling organic liquid diluent solvent from 1-hexene and 1-octene is replaced with the comparatively simple separation of C6 cyclics from 1-octene.

A disadvantage of using the organic liquid diluent solvent as defined in the process of the invention is that the solubility of the Cr catalyst in this type of solvent has been shown to be very low. As such, a separate catalyst solvent in which the catalyst system components are highly soluble and which is compatible with the organic liquid diluent solvent is used to overcome this disadvantage. In this way, the advantages of both catalyst and organic liquid diluent solvent are leveraged in the process of the invention as illustrated, provided that the correct ratio of organic liquid diluent solvent to catalyst solvent is maintained to fulfil the following criteria: there must be sufficient catalyst solvent to ensure that the (typically chrome) catalyst is completely dissolved, but not too much that the catalyst solvent dilutes the organic liquid diluent solvent to the extent that the benefit of higher ethylene solubility in the selected organic liquid diluent solvent is negatively impacted.

The invention claimed is:

1. A process for oligomerising a hydrocarbon to form at least one co-monomer product, the process including
   feeding a hydrocarbon reactant and organic liquid diluent solvent into an oligomerisation reactor which is at an elevated pressure above atmospheric pressure, said organic liquid diluent solvent having a normal boiling point below the normal boiling point of 1-hexene but above −20° C., or said organic diluent solvent being in the form of a solvent admixture with at least 70% by mass of the solvent admixture constituting organic diluent solvents having a normal boiling point below the normal boiling point of 1-hexene but above −20° C., and said oligomerisation reactor holding at least one co-monomer product formed in the oligomerisation reactor admixed with a catalyst system introduced into the oligomerisation reactor, said catalyst system including a catalyst dissolved in at least one catalyst solvent to facilitate introducing said catalyst system into the oligomerisation reactor;

oligomerising at least a portion of the hydrocarbon reactant in the reactor to form said at least one co-monomer product and polymeric by-product as part of a liquid product with the liquid product thus including organic liquid diluent solvent, said at least one co-monomer product, said catalyst system, unreacted hydrocarbon reactant and said polymeric by-product; and withdrawing liquid product which includes organic liquid diluent solvent, said at least one co-monomer product, said catalyst system, unreacted hydrocarbon reactant and said polymeric by-product from the reactor, wherein, when there is only one catalyst solvent and only one organic liquid diluent solvent, said catalyst solvent and said organic liquid diluent solvent are not the same solvent, and when there is more than one catalyst solvent or more than one organic liquid diluent solvent, at least one of the catalyst solvents is not also used as organic liquid diluent solvent or at least one of the organic liquid diluent solvents is not also used at the catalyst solvent, and wherein the mass ratio of all organic liquid diluent solvent introduced into the oligomerisation reactor to all catalyst solvent introduced into the oligomerisation reactor over a selected time period is between 15:1 and 4500:1.

2. The process as claimed in claim 1, in which the mass ratio of all organic liquid diluent solvent introduced into the oligomerisation reactor to all catalyst solvent introduced into the oligomerisation reactor is between 150:1 and 1500:1.

3. The process as claimed in claim 1, which includes feeding the organic liquid diluent solvent into the oligomerisation reactor, such that the mass fraction of the organic liquid diluent solvent in said liquid product on a hydrocarbon reactant free basis is maintained between 0.4 and 0.8.

4. The process as claimed in claim 1, in which the organic liquid diluent solvent is selected from the group consisting of isobutane, isopentane, neopentane, 2-methylpentane, 3-methylpentane, 2,2-dimethylbutane, and mixtures of two or more thereof.

5. The process as claimed in claim 1, in which the catalyst solvent is selected from the group consisting of 1-hexene, 1-octene, cyclohexane, methylcyclohexane, methylcylopentane, methylenecyclopentane, and mixtures of two or more thereof.

6. The process as claimed in claim 1, in which the hydrocarbon reactant is ethylene, the process using a catalyst system which favours tetramerisation of ethylene so that at least 30% by mass of the liquid product formed is 1-octene.

7. The process as claimed in claim 1, which includes treating the withdrawn liquid product to separate co-monomer product and any polymeric by-product from unreacted hydrocarbon reactant and organic liquid diluent solvent, treating the withdrawn liquid product to separate co-monomer product and any polymeric by-product from unreacted hydrocarbon reactant and organic liquid diluent solvent including flashing the withdrawn liquid product in at least one flash stage;

subjecting an overheads vapour stream from the at least one flash stage to at least one distillation operation; and withdrawing the unreacted hydrocarbon reactant and diluent solvent as an overhead stream from the distillation operation.

8. The process as claimed in claim 7, in which the withdrawn unreacted hydrocarbon reactant and organic liquid diluent solvent are recycled together as a single stream to the oligomerisation reactor.

9. The process as claimed in claim 7, in which treating the withdrawn liquid product to separate co-monomer product and any polymeric by-product from unreacted hydrocarbon reactant and organic liquid diluent solvent includes subjecting a bottoms stream from said at least one flash stage to at least one further flash stage which is at a lower pressure than said at least one flash stage.

10. The process as claimed in claim 9, in which the bottoms stream from said at least one flash stage is heated to a temperature of at least 190° C. before being flashed in said at least one further flash stage, and in which the heated bottoms stream from said at least one flash stage is flashed in said at least one further flash stage at a pressure which is at least 2 bar less than an operating pressure of said at least one flash stage so that said at least one further flash stage provides a concentrated polymer bottoms stream which includes most of the polymeric by-product and an overhead vapour stream which includes some unreacted hydrocarbon reactant, some vapourised organic liquid diluent solvent and some co-monomer product, the process further including condensing said overhead vapour stream from said at least one further flash stage and recycling the condensed overhead vapour stream to said at least one distillation operation where any unreacted hydrocarbon reactant and organic liquid diluent solvent are recovered and recycled to the oligomerisation reactor.

11. The process as claimed in claim 10, in which operating conditions of the at least one further flash stage are selected such that said overhead vapour stream from said at least one further flash stage is condensed at a pressure of less than 10 bar(a) with plant cooling water at a temperature of between 20° C. and 40° C., with more than 95% by mass of the unreacted hydrocarbon reactant reporting to the at least one further flash stage being condensed.

12. A process for oligomerising a hydrocarbon to form at least one co-monomer product, the process including feeding a hydrocarbon reactant and organic liquid diluent solvent into an oligomerisation reactor which is at an elevated pressure above atmospheric pressure, said organic liquid diluent solvent having a normal boiling point below the normal boiling point of 1-hexene but above −20° C., or said organic diluent solvent being in the form of a solvent admixture with at least 70% by mass of the solvent admixture constituting organic diluent solvents having a normal boiling point below the normal boiling point of 1-hexene but above −20° C., and said oligomerisation reactor holding at least one co-monomer product formed in the oligomerisation reactor admixed with a catalyst system introduced into the oligomerisation reactor, said catalyst system including a catalyst dissolved in at least one catalyst solvent to facilitate introducing said catalyst system into the oligomerisation reactor, in which the oligomerisation reactor is a bubble column reactor holding said liquid product as part of a bulk liquid phase, and in which feeding a hydrocarbon reactant and organic liquid diluent solvent into the oligomerisation reactor includes feeding into the bulk liquid phase of the bubble column reactor fresh hydrocarbon reactant which has been condensed and said organic liquid diluent solvent and said catalyst system;

oligomerising at least a portion of the hydrocarbon reactant in the reactor to form said at least one co-monomer product and polymeric by-product, in which the oligomerising includes allowing at least a portion of the hydrocarbon reactant and the organic liquid diluent solvent to vapourise to form bubbles rising through the bulk liquid phase, with the hydrocarbon reactant oligomerising to form as part of the bulk liquid phase said liquid product which includes organic liquid diluent solvent, said at least one co-monomer product, said catalyst system, unreacted hydrocarbon reactant and said polymeric by-product, and with the evaporation of both the hydrocarbon reactant and the organic liquid diluent solvent effecting heat removal from the bulk liquid phase, and withdrawing liquid product which includes organic liquid diluent solvent, said at least one co-monomer product, said catalyst system, unreacted hydrocarbon reactant and said polymeric by-product from the reactor including withdrawing some of the bulk liquid phase to maintain the bulk liquid phase at a desired level, wherein, when there is only one catalyst solvent and only one organic liquid diluent solvent, said catalyst solvent and said organic liquid diluent solvent are not the same solvent, and when there is more than one catalyst solvent or more than one organic liquid diluent solvent, at least one of the catalyst solvents is not also used as organic liquid diluent solvent or at least one of the organic liquid diluent solvents is not also used at the catalyst solvent, and wherein the mass ratio of all organic liquid diluent solvent introduced into the oligomerisation reactor to all catalyst solvent introduced into the oligomerisation reactor over a selected time period is between 15:1 and 4500:1;

the process further including allowing gaseous components comprising any unreacted vapourised hydrocarbon reactant and vapourised organic liquid diluent solvent and any oligomerisation product that reports to a vapour phase to disengage from the bulk liquid phase into a head space in the bubble column reactor above the bulk liquid phase;

withdrawing the gaseous components from the head space;

cooling the gaseous components withdrawn from the head space thereby at least partially to condense the gaseous components, forming a vapour fraction and a liquid fraction both of which include an admixture of unreacted hydrocarbon reactant, organic liquid diluent solvent and oligomerisation product;

recycling the condensed liquid fraction to the bulk liquid phase in the bubble column reactor; and withdrawing the vapour fraction.

13. The process as claimed in claim 12, in which fresh gaseous hydrocarbon reactant and optionally recycled vapourised unreacted hydrocarbon reactant and optionally recycled vapourised organic liquid diluent solvent recovered from the withdrawn bulk liquid phase is combined and condensed with the gaseous components withdrawn from the head space before the gaseous components are cooled and condensed, and in which the organic liquid diluent solvent in the bulk liquid phase is selected and maintained at a mass concentration such that, at a bubble column reactor pressure of between 40 bar(a) and 80 bar(a) more than 99.5% by mass of the gaseous components from the head space, fresh gaseous hydrocarbon reactant, any recycled unreacted hydrocarbon reactant and any recycled organic liquid diluent solvent recovered from the withdrawn bulk liquid phase is condensed at a temperature below 35° C.

14. The process as claimed in claim 13, in which said condensation at a temperature below 35° C. takes place at a pressure below the supercritical pressure of ethylene, using an absorption refrigeration system.

\* \* \* \* \*